(12) United States Patent
Rodas

(10) Patent No.: US 10,031,520 B2
(45) Date of Patent: Jul. 24, 2018

(54) SYSTEM AND METHOD FOR PREDICTING AN ADEQUATE RATIO OF UNMANNED VEHICLES TO OPERATORS

(71) Applicant: Maria Olinda Rodas, San Diego, CA (US)

(72) Inventor: Maria Olinda Rodas, San Diego, CA (US)

(73) Assignee: The United States of America, as Represented by the Secretary of the Navy, Washington, DC (US)

( * ) Notice: Subject to any disclaimer, the term of this patent is extended or adjusted under 35 U.S.C. 154(b) by 262 days.

(21) Appl. No.: 15/058,917

(22) Filed: Mar. 2, 2016

(65) Prior Publication Data

US 2016/0252902 A1 Sep. 1, 2016

Related U.S. Application Data

(63) Continuation-in-part of application No. 13/291,211, filed on Nov. 8, 2011.

(51) Int. Cl.
*G05D 1/00* (2006.01)
*A61B 5/18* (2006.01)
*B60K 28/06* (2006.01)

(52) U.S. Cl.
CPC .............. *G05D 1/0027* (2013.01); *A61B 5/18* (2013.01); *B60K 28/06* (2013.01)

(58) Field of Classification Search
CPC ......... G05D 1/0027; B60K 28/06; A61B 5/18
See application file for complete search history.

(56) References Cited

U.S. PATENT DOCUMENTS

| 7,236,861 B2 | 6/2007 | Paradis |
| 2007/0021879 A1 | 1/2007 | DelNero et al. |
| 2007/0233338 A1 | 10/2007 | Ariyur |
| 2009/0326735 A1 | 12/2009 | Wood |

(Continued)

OTHER PUBLICATIONS

Department of Defense, "Network Centric Warfare: Department of Defense Report to Congress," Office of the Secretary of Defense, Washington, DC, 2001.

(Continued)

*Primary Examiner* — Ajay Ojha
(74) *Attorney, Agent, or Firm* — SPAWAR Systems Center Pacific; Kyle Eppele; Arthur K. Samora

(57) ABSTRACT

The present invention is a computer decision tool for use in a system for controlling a team of unmanned vehicles. The computer decision tool includes a system performance model for receiving interface usability, automation level and algorithm efficiency variables and an operator performance model. The operator performance model receives task management efficiency and decision making strategy or DM efficiency variables. The system performance model is responsive to the interface usability, automation level and algorithm efficiency variables for providing a system performance status signal. The operator performance model is responsive to task management efficiency and DM strategy variables for providing an operator performance status signal. An operator capacity decision model is responsive to the system performance and operator performance status signals and a workload variable for providing a decision signal representative of an adequate team size or an optimal recommendation, such as changing the team size.

4 Claims, 21 Drawing Sheets

(56) References Cited

U.S. PATENT DOCUMENTS

2010/0198452 A1 8/2010 Zhang et al.
2010/0228533 A1 9/2010 Cummings
2010/0312917 A1 12/2010 Allport
2011/0118907 A1 5/2011 Elkins

OTHER PUBLICATIONS

H.M. Huang, K. Pavek, B. Novak, J. Albus, and E. Messina, "A Framework for Autonomy Levels for Unmanned Systems (ALFUS)," presented at Proceedings of the AUVSI's Unmanned Systems North America, pp. 849-863, Baltimore, MD, USA, 2005.
D.R. Olsen, Jr., and S.B. Wood, "Fan-Out Measuring Human Control of Multiple Robots", CHI, vol. 6 (1), pp. 231-238, 2004.
M.L. Cummings and P.J. Mitchell. "Predicting Controller Capacity in Supervisory Control of Multiple UAVs," IEEE Systems, Man and Cybernetics, Part A System and Humans, vol. 11(2), pp. 451-460, Mar. 2008.
J.W. Crandall and M.L. Cummings. "Identifying Predictive Metrics for Supervisory Control of Multiple Robots," IEEE Transactions on Robotics—Special Issue on Human-Robot Interaction, vol. 23(5), pp. 942-951, 2007.
M.L. Cummings, C.E Nehme and J.W. Crandall. "Predicting Operator Capacity for Supervisory Control of Multiple UAV," Innovations in Intelligent Machines, vol. 70, Studies in Computational Intelligence J.S. Chahl, L.C. Jain, A. Mizutani, and M. Sato-Ilic, Eds., 2007.
J.W. Crandall and M.L. Cummings. "Developing Performance Metrics for the Supervisory Control of Multiple Robots," presented at Proceedings of the 2nd Annual Conference on Human-Robot Interaction, Washington, DC, 2007.
C.E. Nehme. "Modeling Human Supervisory Control in Heterogeneous Unmanned Vehicle Systems," Ph.D. Thesis, MIT Dept. of Aeronautics and Astronautics, Cambridge, MA, 2009.
Netica Software. Netica Bayesian Belief Network. Norsys Software Corporation (www.norsys.com). Vancouver, BC, Canada.
K. Hedrick, J. Jariyasunant, C. Kirsch, J. Love, E. Pereira, R. Sengupta and M. Zennaro. "CSL: A Language to Specify and Re-Specify Mobile Sensor Network Behavior," 15th IEEE Real-Time and Embedded Technology and Applications Symposium, San Francisco, CA, Apr. 2009.
P.E. Pina, B. Donmez, M.L. Cummings. Selective Metrics to Evaluate Human Supervisory Control Applications. Technical Report HAL Apr. 2008, Massachusetts Institute of Technology, May 2008.
D.R Olsen, S.B. Wood, "Metrics for Human Driving of Multiple Robots", Proceedings of the 2004 IEEE International Conference on Robotics and Automation, Apr. 2004, pp. 2315-2320.
H.A.Ruff, S. Narayanan, M.H.Draper, "Human Interaction with Levels of Automation and Decision-Aid Fidelity in the Supervisory Control of Multiple Simulated Unmanned Air Vehicles", MIT Presence vol. 11, No. 4, Aug. 2002, pp. 335-351.
T.D.Fincannon, A.W.Evans, F.Jentsch, J.Keebler, "Interactive Effects of Backup Behavior and Spatial Abilities in the Prediction of Teamwork Workload Using Multiple Unmanned Vehicles", Proceeding of the Human Factors and Ergonomics Society 52nd Annual Meeting, vol. 52, No. 14, 2008, pp. 995-999.
P. Squire, G.Trafton, R.Parasuraman, "Human Control of Multiple Unmanned Vehicles: Effects of Interface Type of Execution and Task Switching Times", Association for Computing Machinery, Mar. 2006, pp. 26-32.
C.E.Nehme, S.D.Scott, M.L.Cummings, C.Y.Furushi, "Generating Requirements for Futuristic Heterogeneous Unmanned Systems", Human Factors and Ergonomics Society Annual Meeting Proceedings, Jan. 2006, pp. 235-239.
A.D.McDonald, "A Discrete Event Simulation Model for Unstructured Supervisory Control of Unmanned Vehicles", Ph. D. Thesis, MIT Dept of Mechanical Engineering, Cambridge, MA, 2010.
Mark Campbell et al., "Operator Decision Modeling in Cooperative UAV Systems", American Institute of Aeronautics and Astronautics (AIAA), AIAA Guidance, Navigation and Control Conference and Exhibit, Aug. 21-24, 2006, Keystone, CO.
Maria Olinda Rodas, et al., Predicting an Adequate Ratio of Unmanned Vehicles per Operator Using a System With a Mission Definition Language, 2011 IEEE International Multi-Disciplinary Conference on Cognitive Methods in Situaion Awareness and Decision Support (CogSIMA), Miami Beach, FL, 2011.

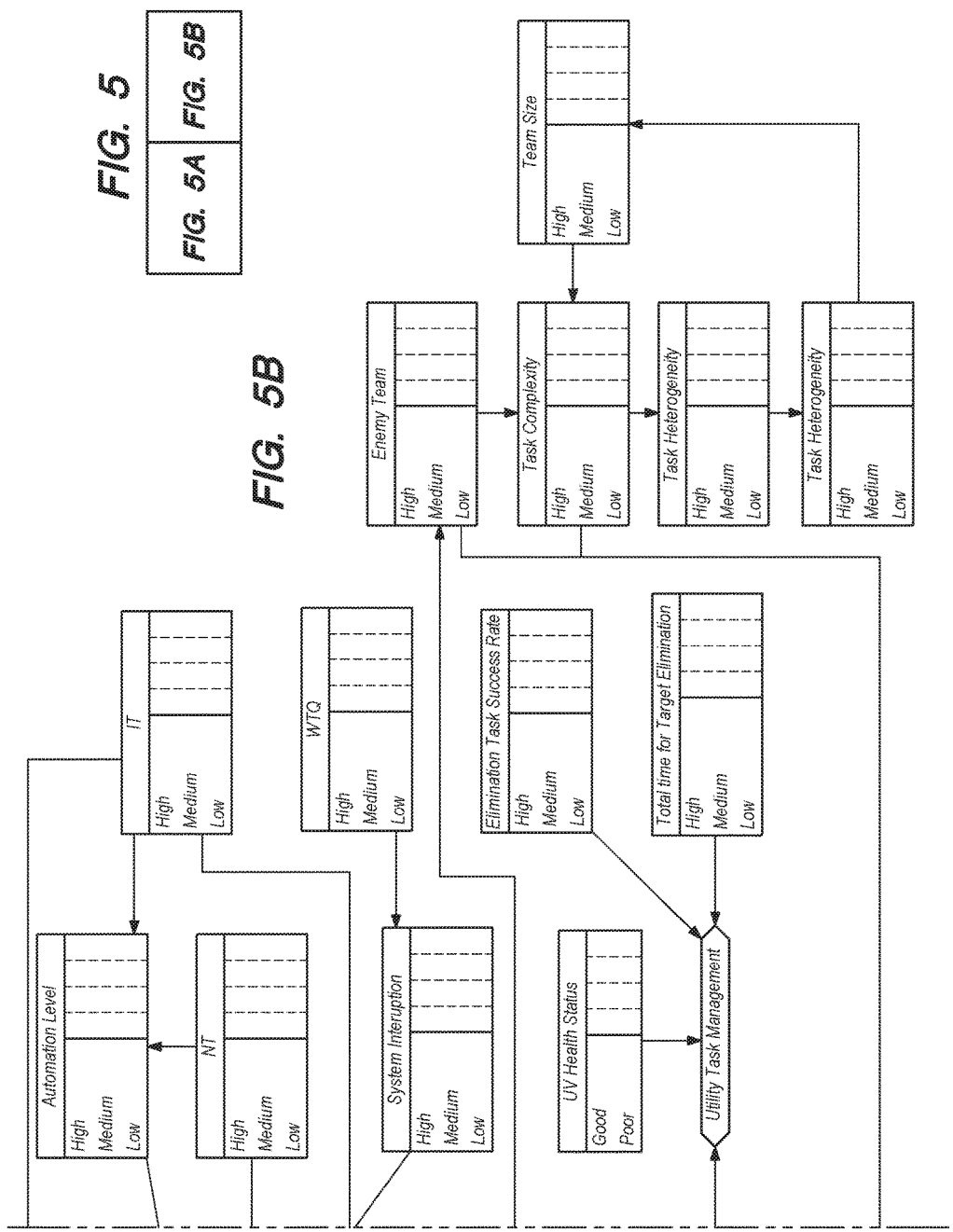

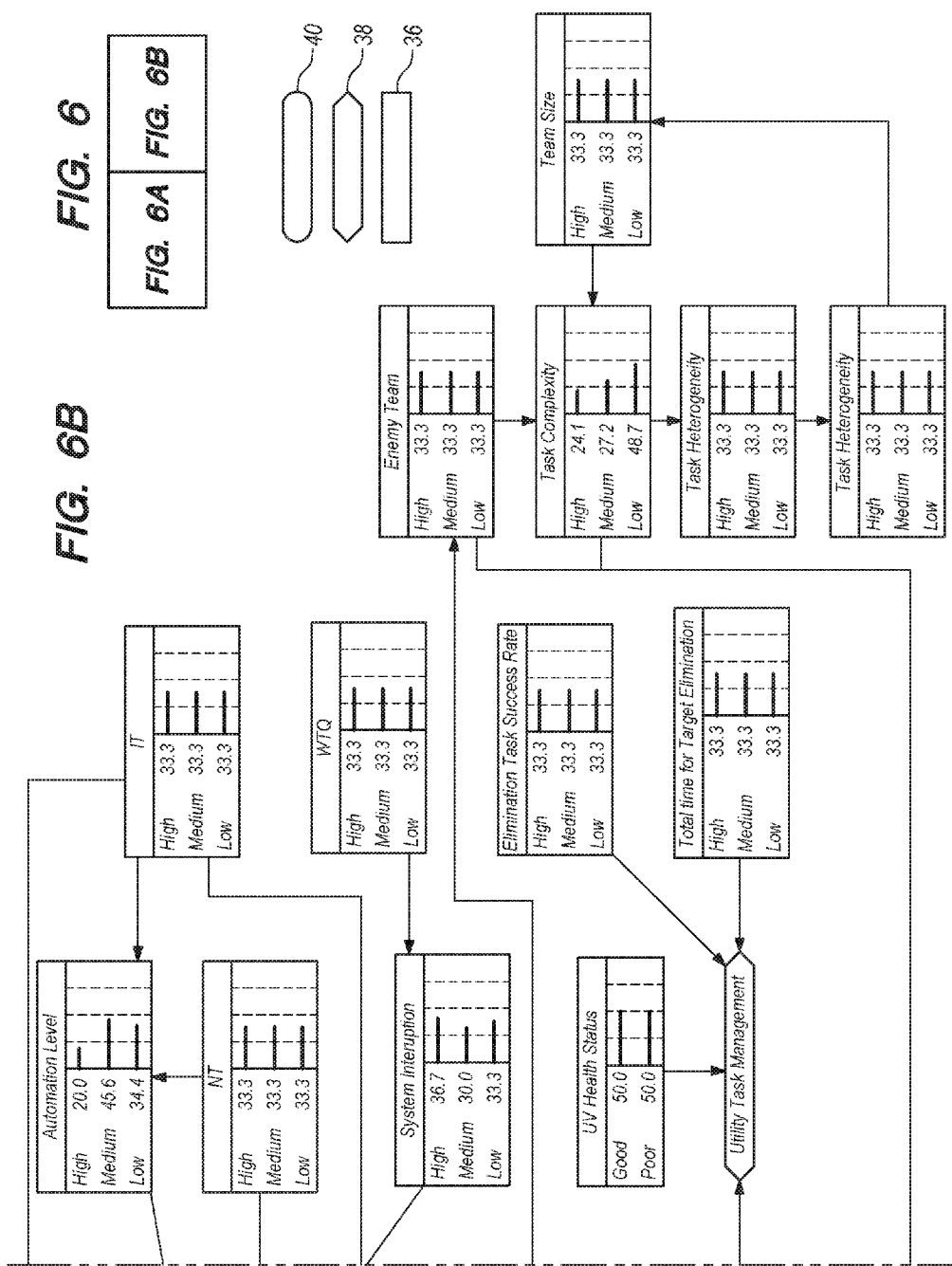

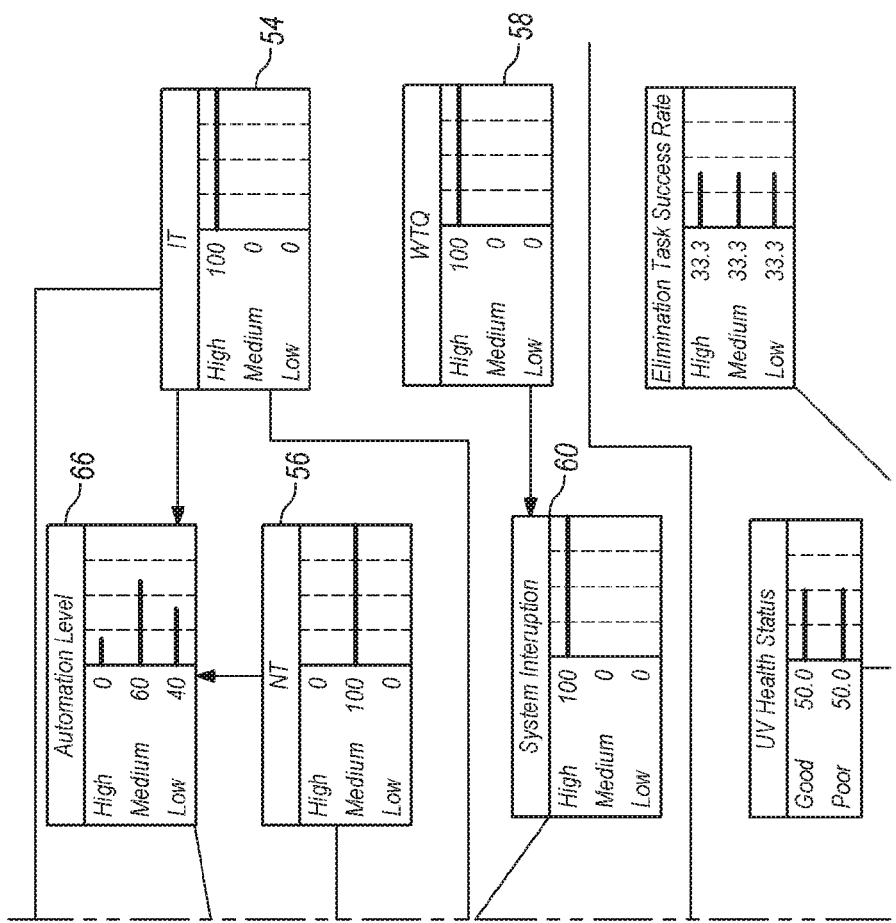

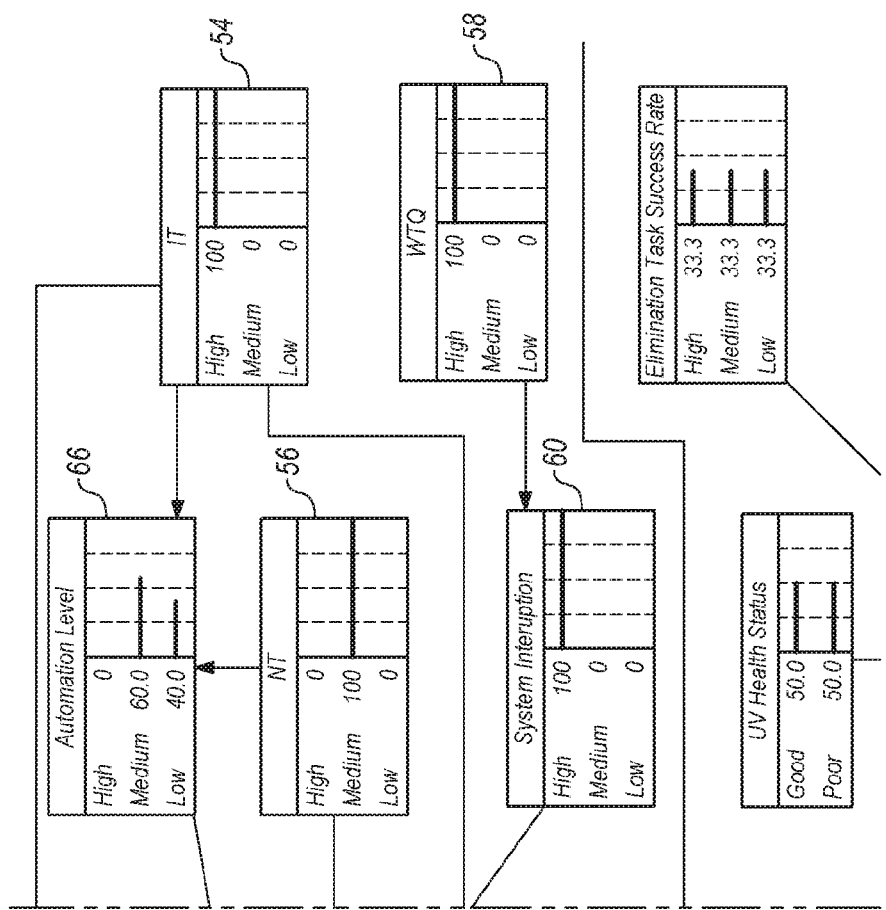

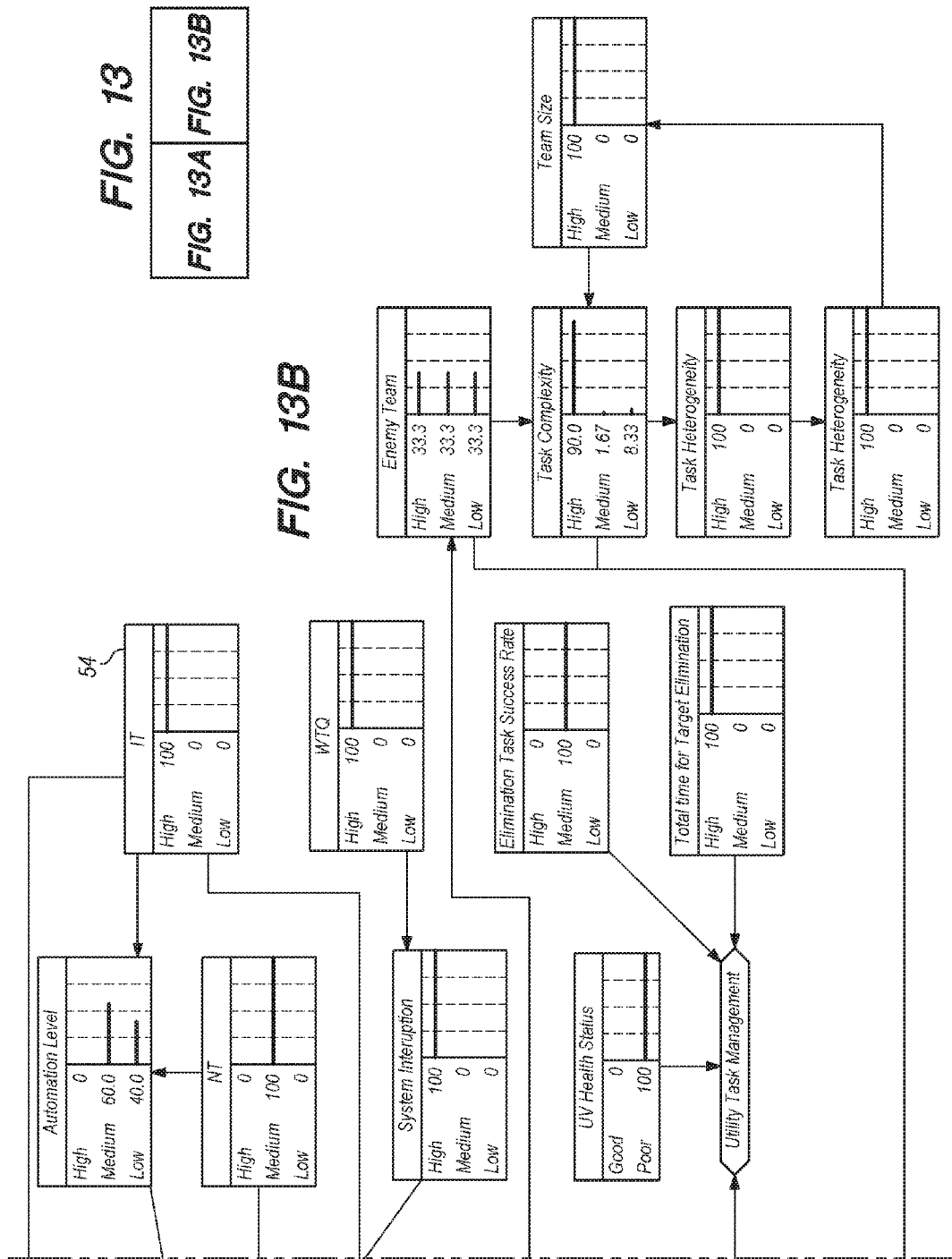

SYSTEM AND METHOD FOR PREDICTING AN ADEQUATE RATIO OF UNMANNED VEHICLES TO OPERATORS

This application is a Continuation-In-Part of U.S. patent application Ser. No. 13/291,211 by Maria Olinda Rodas for an invention entitled "A Computer Decision Tool and Method for Predicting an Adequate Ratio of Unmanned Vehicles to Operators", filed Nov. 8, 2011. The contents of the '211 application are hereby incorporated by reference herein.

FEDERALLY-SPONSORED RESEARCH AND DEVELOPMENT

This invention is assigned to the United States Government and is available for licensing for commercial purposes. Licensing and technical inquiries may be directed to the Office of Research and Technical Applications, Space and Naval Warfare Systems Center, Pacific (SSC Pacific), Code 72120, San Diego, Calif., 92152; voice (619) 553-5118; email ssc_pac_t2@navy.mil, referencing NC 103922.

BACKGROUND OF THE INVENTION

The Department of Defense's future vision for Network Centric Operations (NCO) is intended to increase combat control by networking relevant entities across a battlefield. This new vision implies large amounts of information sharing and collaboration across different entities. An example of a futuristic NCO scenario is one in which a group of heterogeneous Unmanned Vehicles (UVs) are supervised by a single operator using NCO technology. In this type of complex command and control (C2) scenario, UV operators will be subjected to vast amounts of information as compared to today's command and control scenarios.

Therefore, this vision brings with it a new problem that must be addressed: How to maintain an adequate workload to avoid information overload and resulting loss of situation awareness. Currently, C2 technologies that allow the operator to control multiple UVs in a NCO scenario are rapidly increasing. The development of these new C2 technologies generates the tendency to exponentially increase the ratio of UVs to operators. However, if systems are inadequately designed or are used beyond their design capabilities, they will not adequately control for increased workload, which in turn will cause the operator to become overloaded and lose situation awareness. It is critical that decision makers develop predictive models of human and system performance to evaluate the adequacy of a system's design to satisfy specific mission requirements. It would be better to know in advance the optimum team size of UVs for a given mission scenario before it actually occurs, which would allow for improved allocation of UV and operator resources by decision makers.

SUMMARY OF THE INVENTION

In one preferred embodiment, the present invention is a computer decision tool for use in a system for controlling a team of unmanned vehicles. The computer decision tool includes a system performance model for receiving interface usability, automation level and algorithm efficiency variables and an operator performance module interactive or interoperable with the system performance module. The operator performance module receives task management efficiency and DM (decision making) strategy variables (or DM efficiency variables). The system performance module is responsive to the interface usability, automation level and algorithm efficiency variables for providing a system performance status signal. The operator performance module is responsive to the task management efficiency and DM strategy variables for providing an operator performance status signal. An operator capacity decision module is responsive to the system performance and operator performance status signals, as well as a workload variable, for providing a decision signal representative of an adequate team size or an optimal recommendation, such as changing the team size.

BRIEF DESCRIPTION OF THE DRAWINGS

The invention will be more fully described in connection with the accompanying drawings, in which like reference numerals designate like components, and in which:

FIG. 5B also shows other unpopulated data tables of the network of FIG. 5A;

FIG. 6B also shows initially populated nature nodes based on the initial input into the interface usability decision node in FIG. 6A;

FIG. 7B also shows updated nature nodes based on the updated input of nature nodes in FIG. 7A;

FIG. 9B also shows updated probability tables based on the algorithm efficiency node population of FIG. 9A;

FIG. 13B shows updated probability tables for the network of FIG. 5 based on the increase team node population of FIG. 13A; and, FIG. 14 is screen shot, which shows a simulation example for a test scenario that was used to validate the systems and methods of FIG. 1.

DETAILED DESCRIPTION OF THE PREFERRED EMBODIMENTS

Figure 1:
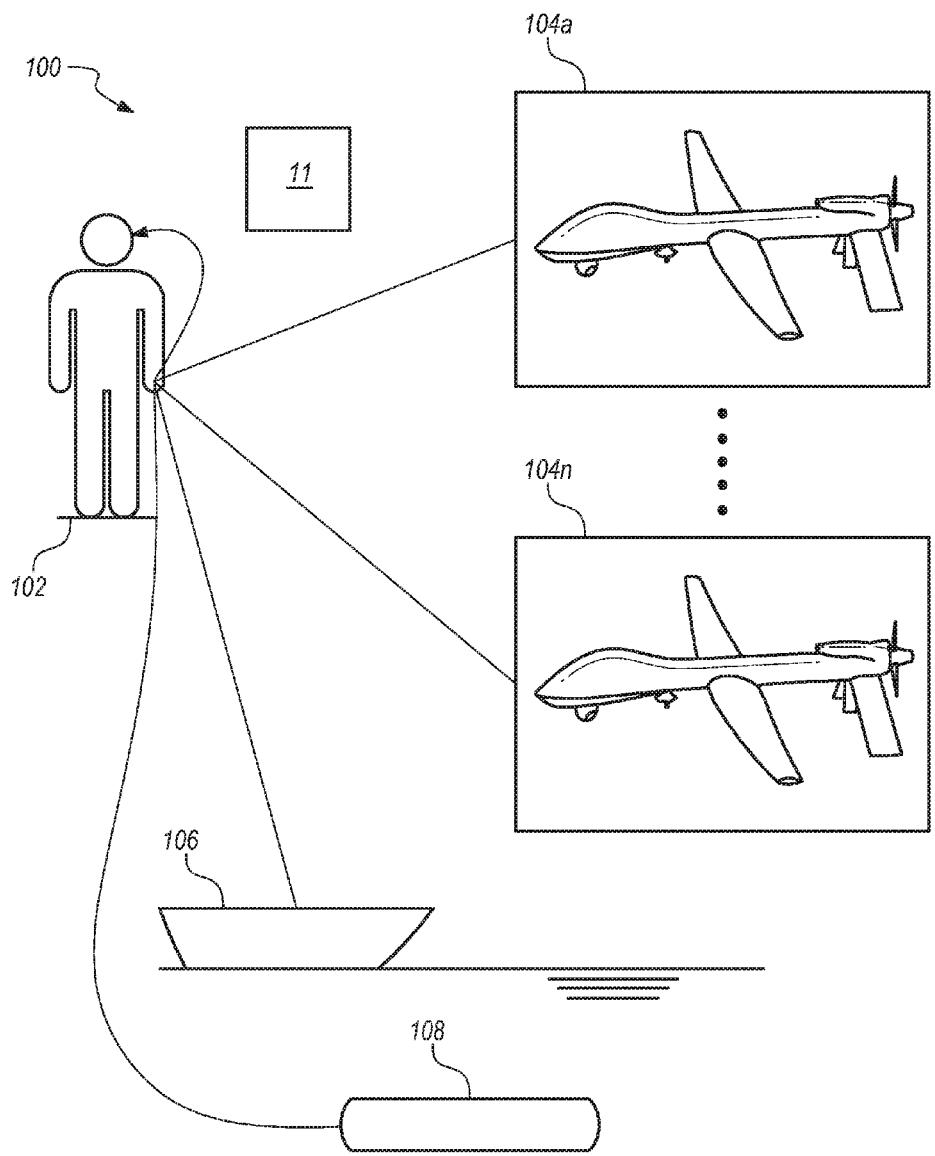
FIG. 1 is a diagram of the system of the present invention according to several embodiments.

In brief overview, the decision tool of the present invention can help decision makers in the Department of the Navy decide whether funded autonomous system's technologies can transition into practical applications for the Navy. The decision tool provides decision makers with a means to evaluate the system's performance under a specific set of decision requirements and realistic mission conditions.

In the operation of unmanned vehicles (UVs), mental workload can be a limiting factor in deciding how many UVs an operator can control or supervise. In the case of one operator supervising multiple vehicles, the operator's workload is measured by the effort required to supervise each vehicle and the overall task. The effort required to supervise an individual UV in a team depends on the efficiency of the system to reduce workload and increase situation awareness. Moreover, workload also depends on the complexity of the mission scenario (the overall task). Some of the characteristics of a complex mission scenario as defined by military standards include: mission time constraints, precision constrains, repeatability in tasks (i.e., navigation, manipulations, etc.), level of collaboration required, concurrence and synchronization of events and behaviors, resource management (i.e., power, bandwidth, ammunition), rules of engagement, adversaries, and knowledge requirements. The degree to which these characteristics are required can also define workload. Consequently, if the system is not designed to achieve specific types of requirements, then when it is tested for those requirements the system may not perform them adequately.

In the prior art, previous attempts to model operator capacity were developed to display temporal constraints associated with the system. The complexity of these measures progressed from measuring operator capacity in homogenous UVs controlled by one operator, to scenarios in which teams of heterogeneous UVs are supervised by one operator. The first prior art equation, the "Fan Out" (FO) equation (Eq. 1), was developed to predict operator capacity in homogenous UVs suggested that the operator capacity is a function of the Neglect Time (NT), or the time the UV operates independently, and Interaction Time (IT), or the time the operator is busy interacting, monitoring, and making decisions with the system.

$$FO = \frac{NT + IT}{IT} = \frac{NT}{IT} + 1 \qquad \text{Eq. 1}$$

Critics of this method suggested that the equation lacked two critical considerations: 1) the importance of including Wait Times (WTs) caused by human-vehicle interaction, and 2) how to link this equation to measure effective performance. Hence, WTs were added to the equation to account for the times the UV has to perform in a degraded state because the operator is not able to attend to it or is not aware of a new incoming event. Three WTs in the prior art were identified: Wait Times due to Interaction (WTI), Wait Times due to Loss of Situation Awareness (WTSA), and Wait Times due to Queue (WTQ).

In the prior art, Carl Nehme from the Massachusetts Institute of Technology (MIT) developed the Multiple Unmanned Vehicles Discrete Event Simulation (MUV-DES). He attempted to create a link to performance by using proxies to measure workload and situation awareness. In this model, Nehme intended to model heterogeneity in UV systems in order to evaluate the system's design. The human was modeled as a server attending to vehicle-generated tasks—both exogenous and endogenous tasks—as defined by their arrival and service processes. The concept of utilization was introduced as a proxy for measuring mental workload. Utilization Time (UT) refers to the percentage of time the operator is busy. The concept of WTSA was used as a proxy to measure Situation Awareness. The UT and WTSA measures were computed as a type of aggregate effect of inefficiencies in information processing rather than being computed as individual measures of workload and situation awareness.

The Nehme model further suggested that many other sources of cognitive inefficiencies, besides these two proxies, are manifested through cognitive delays. The Nehme study emphasized that measures of UT and WTSA are extremely critical to determine supervisory performance and suggested that better methodologies to measure these variables need to be developed.

With the above background in mind, and referring initially to FIG. 1, a diagram of the systems of the present invention according to several embodiments is shown, and is designated by reference character 100. As shown, system 100 can include an operator 102. Operator 102 can be in communication with unmanned aerial vehicles (UAVs) 104a . . . 104n, with unmanned surface vehicles (USVs) 106 and with unmanned underwater vehicles (UUVs) 108. A processor having a medium with non-transitory instructions can be programmed to analyze the interactions between operator 102 and vehicles 104, 106 and 108, in order to predict the optimum number of vehicles 104, 106, 108 that an operator 102 system 100 can control for a given scenario. A library of predictions can be built to allow decision maker to more efficiently allocate resources of operators and UVs 104, 106 108. The manner in which this can be accomplished can be described more fully below.

Figure 2:
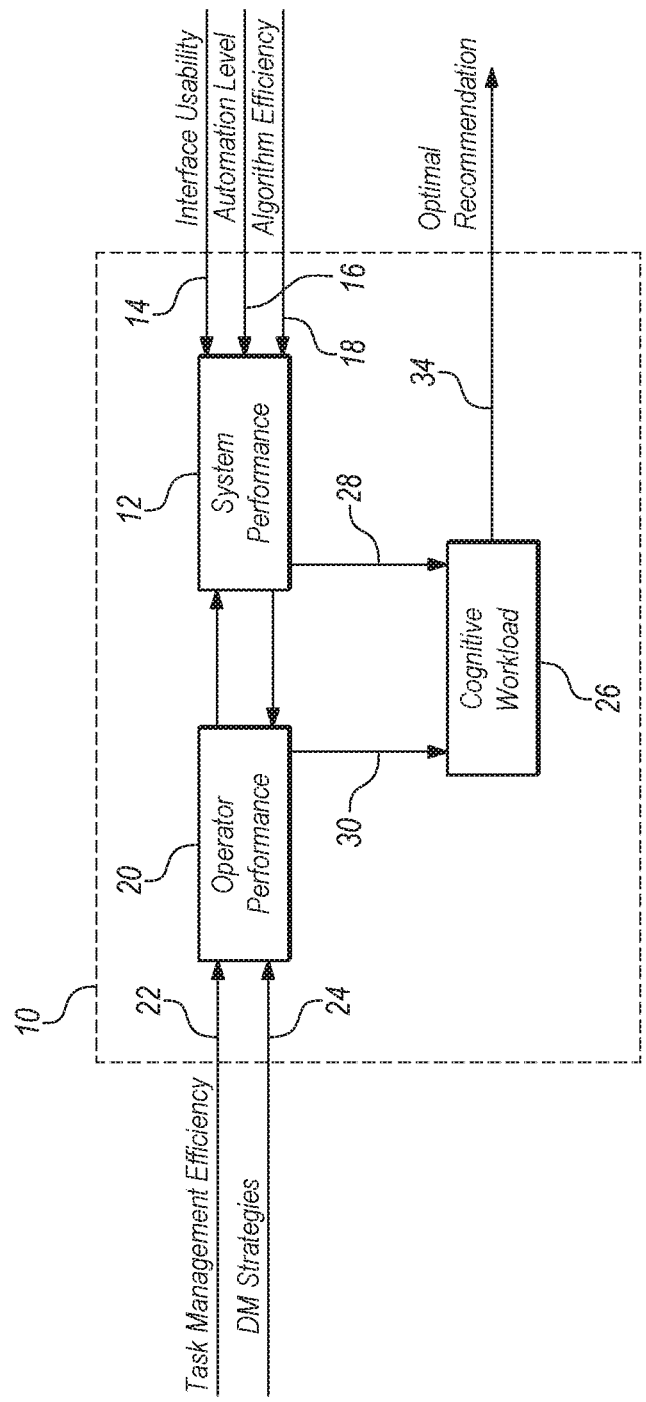
FIG. 2 is a high level representation on the attributes of module captures of the system of FIG. 1.

Referring now to FIG. 2, a high level representation on the attributes of model captures of the present invention is shown. A computer decision tool 10 can be shown in FIG. 2 for use in a system for optimizing a team of unmanned vehicles. The computer tool 10 can include a system performance module 12 for receiving interface usability, automation level and algorithm efficiency variables 14, 16, 18, respectively, and an operator performance module 20, which can be interactive or interoperable with the system performance module 12. The operator performance module receives task management efficiency and decision making (DM) strategy variables 22, 24 (or DM efficiency variables, which can provide a measure of the efficiency of the overall decision making).

The system performance module in FIG. 2 can be responsive to the usability, automation level and algorithm efficiency variables 14, 16, 18 for providing a system performance status signal 28. The operator performance module can be responsive to the task management efficiency and DM strategy variables for providing an operator performance status signal 30.

As shown in FIG. 2, an operator cognitive workload module 26 can be responsive to the system performance and operator performance status signals 28, 30, as well as to a workload variable 32 for providing an adequate capacity or optimal recommendation team size signal 34.

Figure 3:
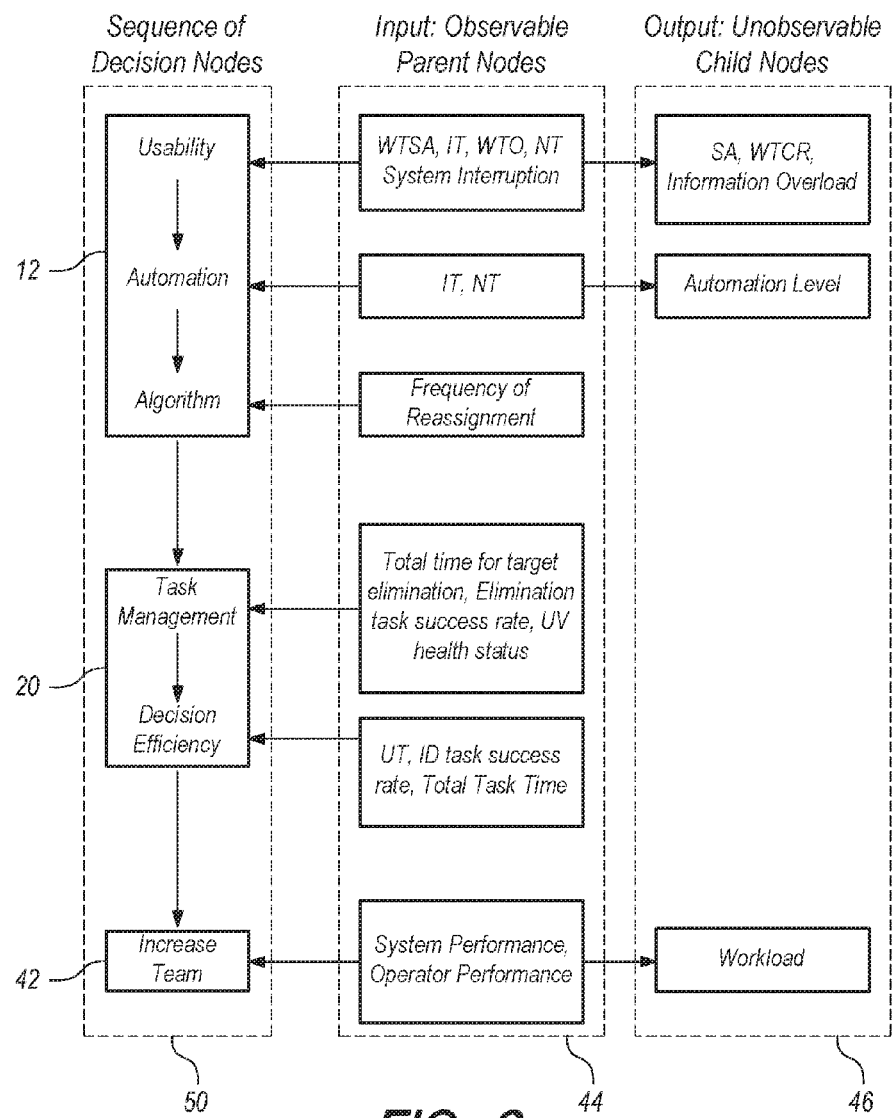
FIG. 3 shows the sequence of decision nodes, the inputs, and the outputs, deducted by the model.

Referring now to FIG. 3, FIG. 3 shows a general decision network representing the decision processes of one embodiment of the present invention. The functions of the various nodes shown in FIG. 3 can be displayed using different shapes and listed in the following Tables 1-4, in which Table 1 displays the Decision Nodes (shape 36), Table 2 displays the Utility Nodes (shape 38), Table 3 displays Observable Nature Nodes (shape 40), and Table 4 displays Unobservable Nature Nodes (shape 40). Unobservable nature nodes can have a functional relationship with its parents; therefore, its values are given as a function of its observable values. For example, if the states of the observable nodes are all true for a specific condition, the unobservable would also be true. The unobservable node can be assigned a value, which is determined by its parent observable. In one embodiment, the decision network representing the decision process involved in deciding whether to increase a particular team size.

TABLE 1

Decision Nodes

| Decision Node | Answer the question... | Function |
|---|---|---|
| Interface Usability | Is the usability of the system adequate to maintain SA? | Tests the usability of the system design. |
| Adequate Automation | Is the automation of the system adequate for the mission scenario? | Tests the automation area of the system design. |
| Algorithm Efficient | Does the operator trust the system? | Tests the operators trust in the system. |
| Tasks Management Efficiency | Is the operator tasks management deficient? | Tests whether the operator technique to manage multiple tasks is efficient. |
| Operator Decision Making Efficiency | Is the operator overall decision making efficient? | Tests the overall efficiency of the operator decision making during the trial. |
| Increase Team | Can we increase our current team? | Tests whether the system can be increased. |

TABLE 2

Utility Nodes

| Utility Node | Corresponding decision node | Function |
|---|---|---|
| Utility Interface | Interface Usability | Determines the preferences/utilities of the decision maker in respect to the interface usability decision. |
| Utility Automation | Adequate Automation | Determines the preferences/utilities of the decision maker in respect to the adequate automation decision. |
| Utility System DM | Algorithm Efficient | Determines the preferences/utilities of the decision maker in respect to the algorithm efficient decision. |
| Utility Task Management | Task Management Efficiency | Determines the preferences/utilities of the decision maker in respect to the task management efficiency decision. |

TABLE 2-continued

Utility Nodes

| Utility Node | Corresponding decision node | Function |
|---|---|---|
| Utility Operator DM | Operator Decision Making Efficiency | Determines the preferences/utilities of the decision maker in respect to the operator decision making efficiency decision. |
| Utility of Capacity | Increase Team | Determines the preferences/utilities of the decision maker in respect to the increase team decision. |

TABLE 3

Observable Nature Nodes

| Observable Nature Node | Function |
|---|---|
| Wait Times due to Loss of Situation Awareness (WTSA) | Measures the time the operator losses situation awareness of a vehicle trajectory intersecting or crossing a hazard area. |
| Neglect Time (NT) | Measures the autonomy of a system or vehicle. |
| Interaction Time (IT) | Measures the time the operator spend interacting with the system, waiting for information and making decisions to accomplish tasks. |
| Wait Times due to Queue (WTQ) | Measures the time a vehicle or event needs to wait to be served because the operator is busy attending another task. |
| Utilization Time (UT) | Measures the time the operator spend interacting with the system, it does not include waiting for information and/or time spends in decision making. |
| System Interruption | Measures the time the operator is interrupted because a new queue enters the system. |
| Elimination Task Success | Measures the number of enemies being eliminated from the total number of enemies correctly identified. |
| UV Health Status | Measures the health of each UV (damage is caused by exposure to hazard areas) |
| Total Time for Target Elimination | Measures the average time to eliminate enemies during the trial. |
| Team Size | Specify the size of the team (3 possible) |
| Team Heterogeneity | Specify the level of heterogeneity of the team (3 available) |
| Frequency of Reassignment | Measures the number of times the operator has reassign a task previously assigned by the system. |
| Total Task Time | Measures the total time that takes to complete the trial. |
| ID Success Rate | Measures the number of vehicles being correctly identified. |

TABLE 4

Unobservable Nodes

| Unobservable Node | Function |
|---|---|
| System Performance | Measures the outcomes of the decisions within the system performance sub-module to inform the operator performance sub-module. |
| Information Overload | Measures the degree of information overload. |
| Situation Awareness (SA) | Measures the operator' situation awareness. |
| Workload | Measures the cognitive workload experience by the operator. |
| Wait Times due to Cognitive | Measures the time to acquire the right mental module once the operator switches his/her attention |

TABLE 4-continued

Unobservable Nodes

| Unobservable Node | Function |
|---|---|
| Reorientation | to a secondary task. |
| Automation Level | Measures the level of automation of the system. |
| Operator Performance | Measures the outcomes of the decision within the operator performance and the system performance sub-modules to inform the workload sub-module. |
| Task Complexity | Measures the complexity of the mission scenario. |
| Enemy Team | Measures the size of the enemy team. |
| Task Heterogeneity | Measures the tasks heterogeneity during the trial. |

Referring now to FIG. 3, FIG. 3 shows an example of data flow of one embodiment of the present invention, including where the data comes from, which information is being input into the model and which is being output.

The Sequence of Decision Nodes column displays a sequence of hierarchical decision making nodes. The first three Utility, Automation and Algorithm nodes that are within the first box represents the decision being made in the first, system performance sub-model 12 of FIG. 2.

The next two Task Management and Decision Efficiency nodes within the second box represent the decision being made in the second, operator performance sub-model 20 of FIG. 2.

The Increase Team box 42 shown in FIG. 3 can represents the final decision. Box 42 can be used to represent how the systems and methods of the present invention can represent a sequence and hierarchical decision making process.

Figure 4:
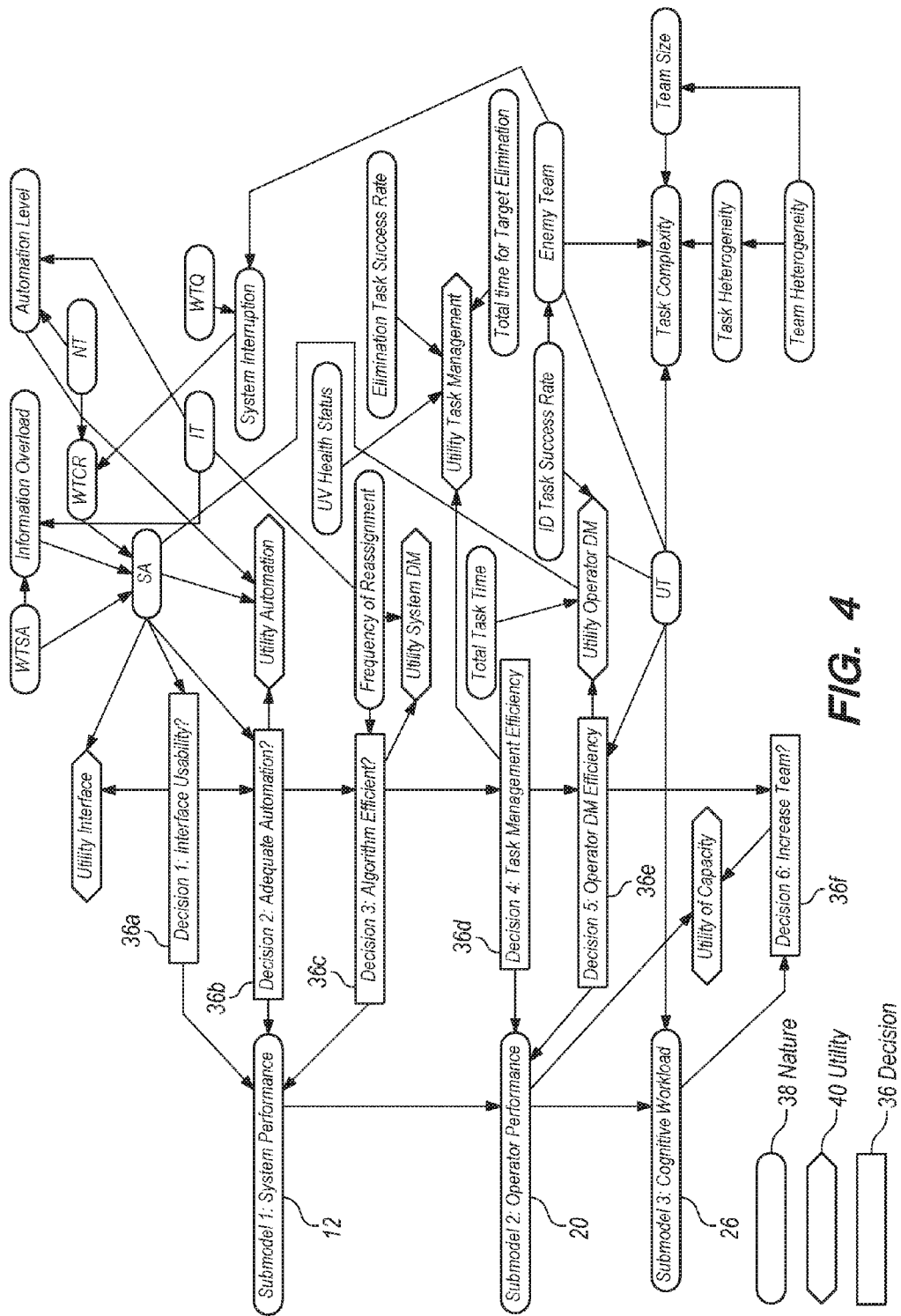
FIG. 4 shows a general decision network representing the decision processes of one embodiment of the present invention, and how the processes relate to each other.

The Input: Observable Parent Nodes column 44 can represent observable nodes/measures that can be gathered from the experimental trials/simulation to serve as an input in each single decision. The Output: Unobservable Child Nodes column 46 shown in FIG. 4 represents the output of the model in terms of other variables being computed (besides the outcome of each single decision node). The arrows can represent input being used for the respective node. For example, for the automation level node, what is observed can be used for the model to compute and optimize the decision of whether the system has an adequate level of automation are IT and NT observations.

From FIG. 3, it can be seen that within the automation decision node (column 50), IT and NT can be observed and can be first used to compute the unobserved nodes. When unobserved nodes, in this case automation level, is being computed, then the network moves into computing the outcome of the automation decision node. A detailed example follows below.

The systems and methods of the present invention can model operator capacity in a complex mission scenario in a manner that can converge all previous research in the area, to create a more comprehensive model of operator capacity. The more comprehensive model of the present invention can fill in the gaps of current research by introducing new variables and relationships to previous models. The model can be constructed in a way so prior knowledge about the relationship between variables can serve to better predict missing data, such as workload and situation awareness. Moreover, the model can be structured in a way that will make it easy to determine which areas in the system design need improvement. The ultimate goal of this study is to develop a decision-making tool that can function to evaluate and determine the effectiveness and limitations of a particular NCO technology for a particular complex mission scenario. The tool can be operated for a plurality of scenarios and a library of recommended teams sizes based on the NCO technology, the operator and the scenario can be built to allow planners/decision makers to more efficiently allocate UV and operator resources.

1. Approach

The approach taken by this research study was to model the decision-making process required to decide whether to increase a particular team size (as defined herein, team size can be taken to mean the total number of UAVs 104, USVs 106 and UUVs 108 proposed for control by human operator 100. This approach was taken in order to present decision makers with a decision-support tool that will ensure that knowledgeable decisions are made in regards to the adequacy of a given team size with a particular NCO technology. Modeling the decision-making process, as opposed to the environment, can allow for more knowledgeable decisions because not only are the most important factors in the decision taken into account, but optimization of the recommended decision's outcome can also be possible. This approach can provide adequate information to the user to make a decision. And while the model is based on answering this particular question, the nature of the situation is manifested in the model, thus allowing users to draw more conclusions than only the adequacy of the team size.

2. The Model

Referring now to FIG. 4, the decision network of the present invention can model the decision-making process required to decide whether to increase a given team size with the selected NCO technology. More specifically, Netica® Software can be used to develop a Bayesian decision network that incorporates quantitative and qualitative information about the model. This Netica® software can be chosen mainly because it can accommodate missing or incomplete data. Using Netica® software can allow researchers to compute unobservable variables (i.e., missing data) based on measures that are observed (i.e., prior knowledge). However, other software with similar functionality could be used to accomplish the methods of the present invention.

A decision network can consist of nature, decision, and utility nodes. Nature nodes can represent variables over which the decision maker has no control. Decision nodes can represent variables over which the decision maker can make a decision. Utility nodes can represent a measure of value, or the decision maker's preferences for the states of the variables in the model. Tables 1-4 above list the sorts of nature (observable and unobservable), decision and utility nodes that are accounted for the systems and methods of the present invention.

In this type of network, the outcome of a decision node is maximized by finding a configuration of the various states of the sets of variables that maximize the values of the utility node. Therefore, based on a series of requirements, or utility values, a decision network provides the user with the correct decision. Additionally, the arrows in the model represent reasoning relationships and are detailed in conditional probability tables (CPTs) of the nature and utility nodes. In the CPT, the distribution of each node will be determined a priori based on the relationships specified in each conditional probability. The CPTs represent the relationship between the does that can be gathered by experience or can be data driven. The CPTs are not shown in the Figs. for clarity; however, the CPTs can be seen when Netica® software is used by clicking on the respective nodes, as described more fully below and shown in screen shot 88 in FIG. 14.

3. Model Assumptions

This model makes several assumptions. First, the type of UV system addressed by this model is one in which a single human operator is responsible for supervising a team of heterogeneous UVs. The human operator is assumed to act in a supervisory control style, interacting with the system at discrete points in time (i.e., there is no manual control). Second, in this model, the human operator is responsible for supervising a team of heterogeneous UVs defending an oil platform from potential enemies. Third, the human operator could be situated in a ground-based, sea-based, or airborne control station. Fourth, the model can be built in a way such that decision makers will use this model to help them decide if a particular technology is adequate for specific mission requirements. Finally, the model assumes that the decision making process required to make this decision is hierarchical; therefore, later decisions are based on earlier ones. The model captures attributes from the Operator Performance Model, the System Performance Model, and the Operator Capacity Model as shown in FIG. 2.

4. Model Description

Referring again FIG. 4, the model can be based on three major areas of relevance for the decision to increase the team size: system performance 12, operator performance 20 and cognitive workload 26 (See FIG. 2). These areas of relevance can be represented in the model as sub-models; each of them contains one or more decision nodes that correspond to the decisions that must be made by the operator in each area to ensure that they are working adequately. The order in which the decision nodes have been organized represents the way in which decisions should be made (see the Decision 1-6 nodes 36a-36f shown in FIG. 4). The model represents a sequence of decisions in which later decisions can depend on the results of earlier ones. In this model, the last decision is shown at the end of the sequence. The last decision (Decision Node 36f in FIG. 3) can determine whether the team size should be increased.

The system performance sub-model 12 can include three decision nodes with the followings decisions: 1) Decision Node 1 (block 36a in FIG. 4)—Is the interface effective? 2) Decision Node 2 (block 36b)—Does the system have an adequate level of automation? 3) Decision Node 3 (block 36c)—Are the system algorithms efficient for the task? These three decisions (Decisions nodes 36a-36c) can be included in this system performance sub-model 12 because they are representative of areas that are important to ensure good system performance.

As an example of the above, if and NCO technology has good interface usability, the situation awareness (SA) of the operator will be high. But if SA (node 36a) is not high, the system's automation level must be somehow more effective to avoid loss of situation awareness and/or complacency. Then, to ensure that the mission requirements are satisfied, the algorithms used must be working efficiently (node 36c) toward achieving the mission goal. This efficiency can be measured by the number of times the operator reassigns a mission that can be previously assigned by the system, with a lower number signaling higher efficiency. Note that algorithm efficiency is defined in this model only as a result of the operator's perceived trustworthiness of the system. If the system is not perceived as trustworthy, then the operator will tend to override the system frequently and the algorithm efficiency will be low.

The second sub-model shown in FIG. 4, operator performance 20, can be used to ensure that the operator performs effectively with the system being evaluated, as more UVs 104, 106, 108 are introduced to the team, and as the mission scenario can change or can become more complex. Since this is a supervisory control environment, operator performance 20 can be defined in terms of the operator's decision making. There are two decisions (decision nodes) that are important to evaluate whether the operator's performance is adequate for the task: 1) Decision 4 (block 36d)—Is the operator's task management strategy efficient? 2) Decision 5 (block 36e in FIG. 4)—Is the operator's decision making efficient? The first decision 36a (Decision 4) can be necessary to evaluate whether operators will efficiently prioritize different tasks that arrive simultaneously. The second decision (Decision 5) is necessary to evaluate whether the operator will successfully achieve the goals of the mission (i.e., protecting the asset from enemy attack). Together these two decisions summarize what is important to ensure a satisfactory operator performance. Please note that by measuring task management efficiency (node 36d), an attention inefficiency component can be introduced into and measured by the systems and methods of the present invention (i.e., if the task management efficiency increase, a decrease in attention inefficiency can be inferred therefrom).

Finally, the last sub-model shown in FIG. 3, cognitive workload 26, can include the final decision node 36f, "Increase Team?" For this decision, it can be important to ensure that operators are not overloaded, but instead their workload is adequate to successfully complete the mission scenario. This final decision node is the end of a sequence of decisions and therefore it depends on the outcomes of the previous decisions made in the system performance and operator performance sub-models. Stated differently, because of the hierarchical nature of the system, node 36b depends on the outcome of node 36a, node 36c depends on the outcome and/or repopulation of nodes 36a and 36b, and so on through node 36f.

Hence, in order to avoid cognitive overload, not only does the system have to efficiently perform in the mission scenario, but the operator also has to perform efficiently to ensure that tasks are adequately managed and do not overload the operator. The cognitive workload and operator performance sub-models are strongly associated. If cognitive workload is too high, then the operator performance will be low. Therefore, the more inadequate management and tactical decisions operators make, the higher their workload will be.

System performance, operator performance, and cognitive workload are the foundation of this model. Variables such as "Information Overload" and "System Interruption" were included to emphasize the need to evaluate these aspects of the usability of the system (see FIG. 3) in complex supervisory control tasks. These variables are relevant because they contribute to design interfaces, especially in the supervisory control environment in which large amounts of information, and large event queues can result in information overload and frequent system interruptions.

5. Model Measures

The model tool of the present invention can allow for measurement of several output variables. These variables include those implemented in the MUV-DES model of the prior art, as well as specific user-defined metrics that the model can allow to capture. Temporal measures such as UT and WT can be used because they are critical in a system where the operator has limited attention resources that must be divided across multiple tasks. UT can be used to capture the effects of alternate design variables on operator workload. Some researchers in the prior art indicate that average UT and WT can allow for benchmarking and comparison to be made across applications. The level of autonomy in the model is captured through the NT.

In addition to the basic metrics inherently captured by the MUV-DES model, this systems and methods of the present invention can also capture mission-specific metrics. Some of the mission-specific metrics include the rate at which tasks are successfully completed, the UVs' health status and the total time to complete the mission scenario. Furthermore, other measures being captured by the model include Information Overload, System Interruption, and Reassignment Rate. These three measures are important to evaluate the system performance. Information Overload and System Interruption are shown to be related to SA; therefore, they are used to help determine Situation Awareness (SA). The mission specific variables for a given scenario can allow for increased predictive capacity of the computer tool of the present invention.

For example, when the operator is overloaded with information, he/she may not able to focus on what is important; therefore, vital SA can be lost. Moreover, when the system is constantly interrupting the operator at any point in time, it drives the operator's attention away from one task to focus on another, therefore affecting their SA. The system's Frequency of Reassignment measure is used to evaluate the number of times the operator overrides the system. Identifying the amount of times the system has been overridden can help the decision maker determine how trustworthy the system is for the operator. The underlying assumption is that the more the operator overrides the system, the less reliable the algorithm for the system is. For a list of the performance measures used in the model, see Table 5 below.

TABLE 5

Performance Measures

| Performance Measures | MUV-DES (Prior Art) | Present Invention |
|---|---|---|
| Wait Times due To Situation Awareness (WTSA) | x | |
| Wait Times due to Queue (WTQ) | x | |
| Wait Times due to Cognitive Reorientation (WTCR) | x | |
| Interaction Times (IT) | x | |
| Neglected Times (NT) | x | |
| Utilization Times (UT) | x | |
| Total Task Time | x | |
| Information Overload | | x |
| System Interruption | | x |
| Target Elimination Task-Success Rate | | x |
| Identification Task-Success Rate | | x |
| Frequency of Reassignment | | x |
| UV Health Status | | x |

Table 5 above shows performance measures used in the model. Notice Table 5 divides measures that are being used from the MUV-DES model and other measures that were developed specifically for this tool of the systems and methods of the present invention.

Figure 5A:
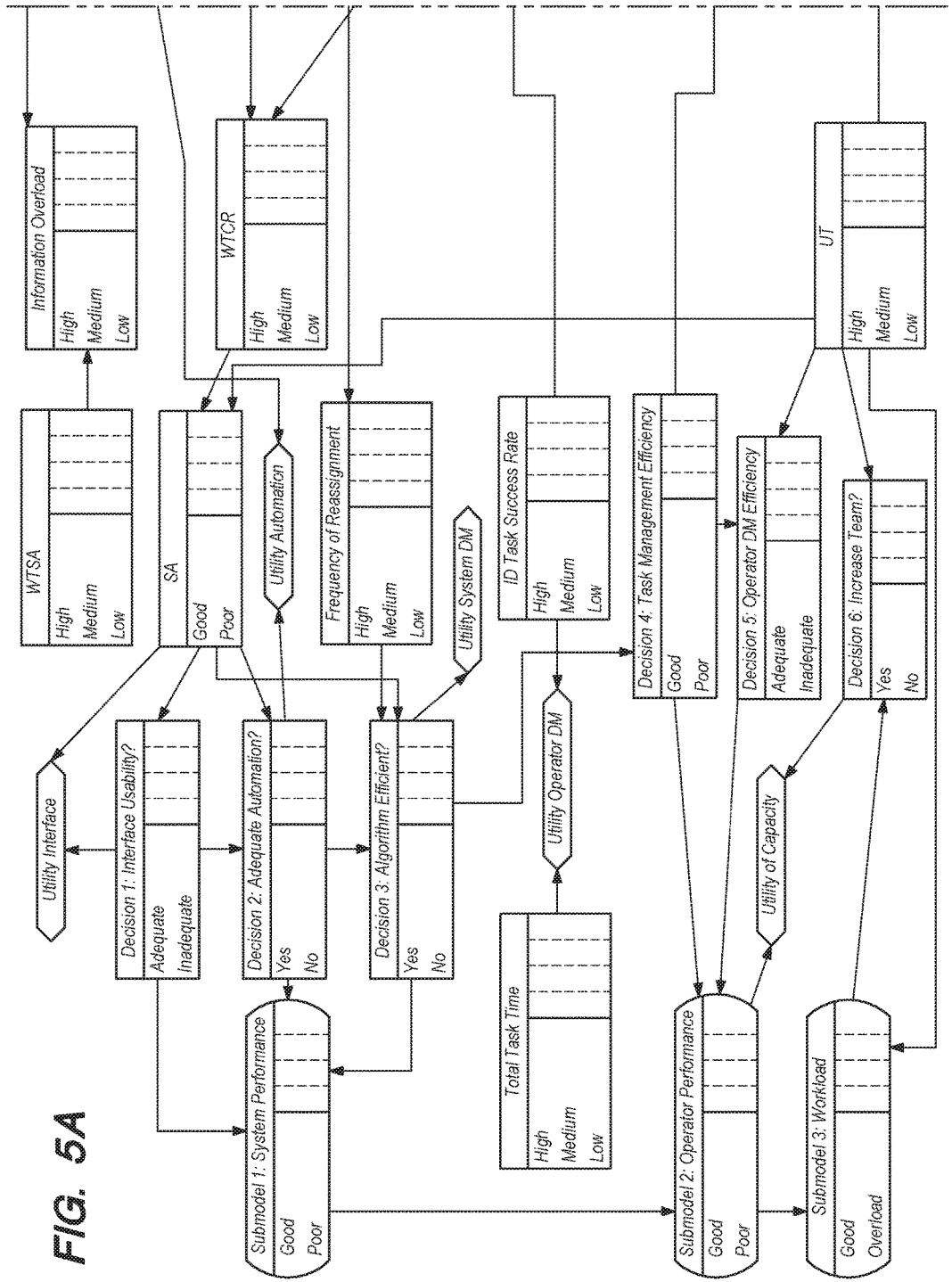
FIG. 5A shows the utility nodes and decision nodes of the network of FIG. 4 in greater detail, with unpopulated data tables, prior to operation of the computer tool.

Referring now to FIG. 5 (FIGS. 5A-5B), FIG. 5 can illustrates the model without observed data and without being compiled (i.e. with blank CPT's under each node). This can be the starting point for the decision making process evaluation. FIG. 5 can show the states on each node, but the CPT tables are not shown at this point because data has not yet been entered into the CPT tables. It should also be noticed and appreciated that CPT tables drive successive computations as they are being used as guidelines. Node 36b was determined based on the determination and subsequent repopulation of node 36a.

Figure 6A:
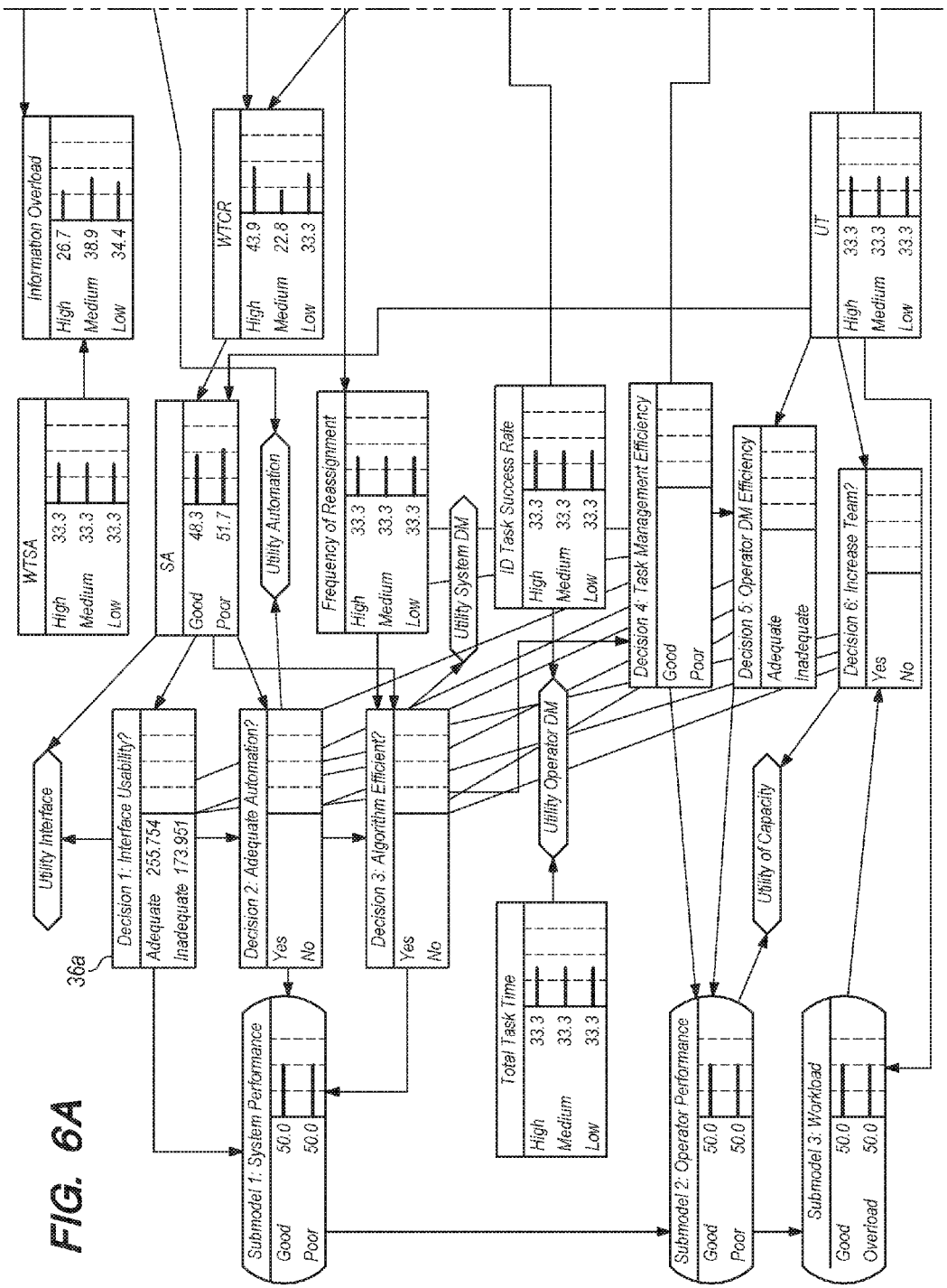
FIG. 6A shows the portion of the network of FIG. 5 related to the interface usability decision nodes based on an initial input into the interface usability decision node.

FIG. 6 (FIGS. 6A-6B) can display the model of the present invention according to several embodiments once operation of the systems and methods of the present invention have begun, including a compilation by a processor by the system. Note the extra arrows (compared to FIG. 4) that have been added as a result of the compilation, indicating the relationship between variables that have not previously being defined. Also, notice that the probabilities display in the first decision node 36a (Interface Usability) are the results of what is called the "most probable explanation"; that is, the results of compiling the net without entering any observed data.

Figure 7A:
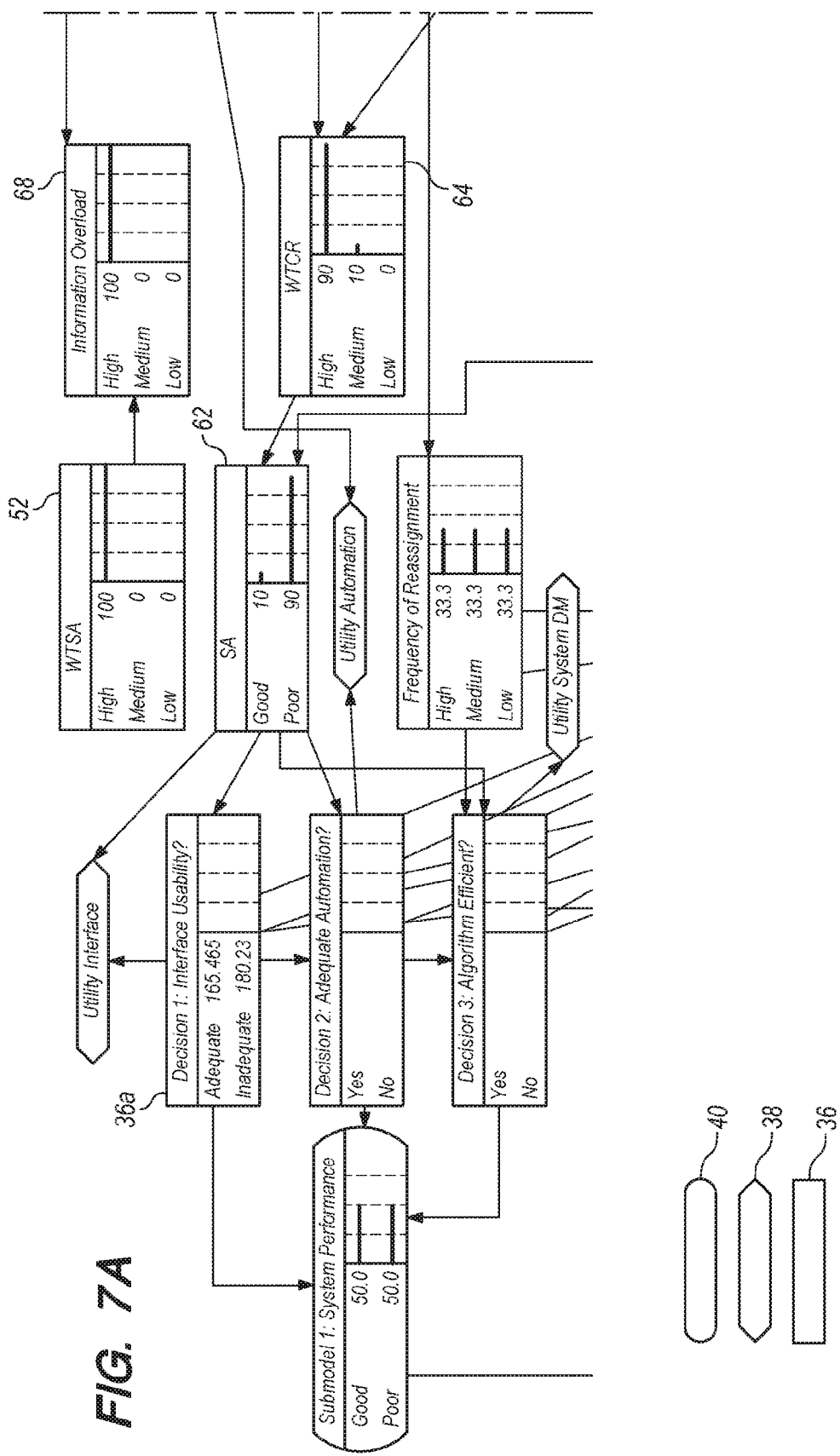
FIG. 7A shows the portion of the network of FIG. 5 related to the updated interface usability decision node once data related to observable nature nodes are input into the network.

FIG. 7 (FIGS. 7A-7B) can display the model once data have been entered in the observables nodes related to the first decision node 36a. The observable nodes WTSA 52, IT 54, NT 56, WTQ 58 and System Interruption 60 can be used to compute the related (children) unobservable nodes: SA 62, WTCR 64, Automation Level 66 and Information Overload 68. The first decision node 36a, Interface Usability, shows a probability for each node status. These probabilities indicate the likelihood that each state of the node will be true, based on the observations entered in the net. In FIG. 7, the highest probability can be seen in the Inadequate node status, which indicates that likelihood that the interface is inadequate given the observations is 180%, as opposed as the status of the interface being adequate (only 165%). It should be appreciated that the percentages notation does not formally indicate a percentage, but functions more as a guidelines as to which outcome is more likely (with the higher percentage number denoting the more likely outcome). It should also be noticed that the decision maker requires making a decision first, in order to move forward in the process and get recommendations for the following decision nodes. Remember, the systems and methods of the present invention can be a hierarchical decision net, therefore decisions are made in an order, probabilities for later decisions will not been displayed until earlier decisions are made. Once the user clicks on "inadequate" in node 36a.

Figure 8A:
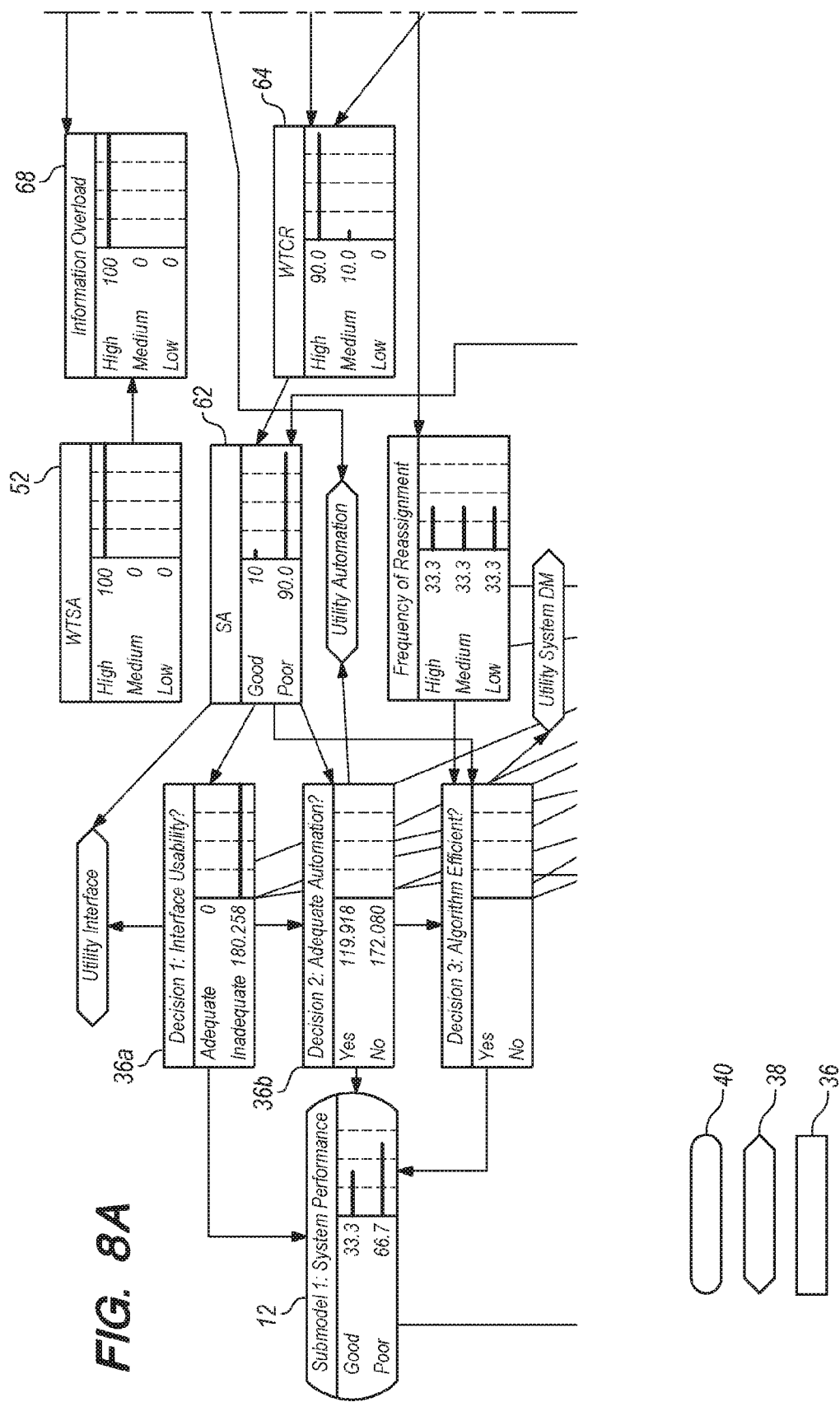
FIG. 8A shows the portion of the network of FIG. 5 related to the adequate automation decision node, based on the usability decision node of FIG. 7A.
Figures 8, 8B:
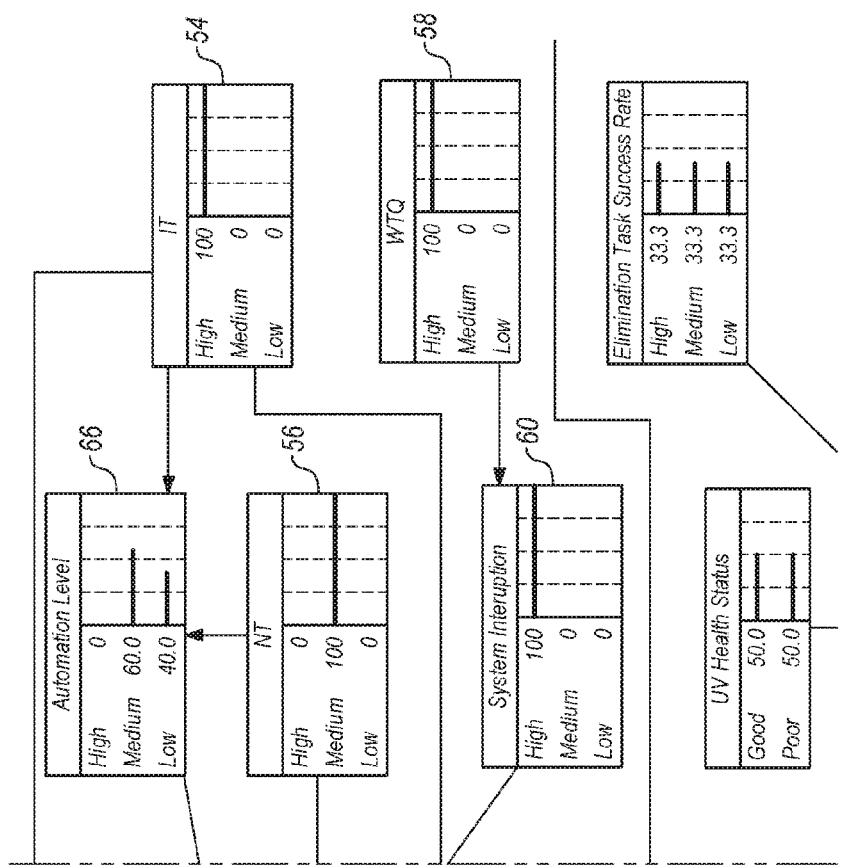
FIG. 8B also shows updated probability tables based on the initial adequate automation node population of FIG. 8A.

FIG. 8 (FIGS. 8A-8B) can display the net once that the decision maker has entered his/her decision outcome for the decision first node (Interface Usability). Note that because as decision has been made and entered in decision node 36a, the probabilities for each node status in 36a and 36b have been computed (in the case of node 36a, because the decision has been made, the node has been repopulated). In this case, the net is recommending that the automation is not adequate (172% versus 120%). Note that the percentage is simply a way of showing the recommendation (the higher number in the node 36 is the recommendation)

Figure 9A:
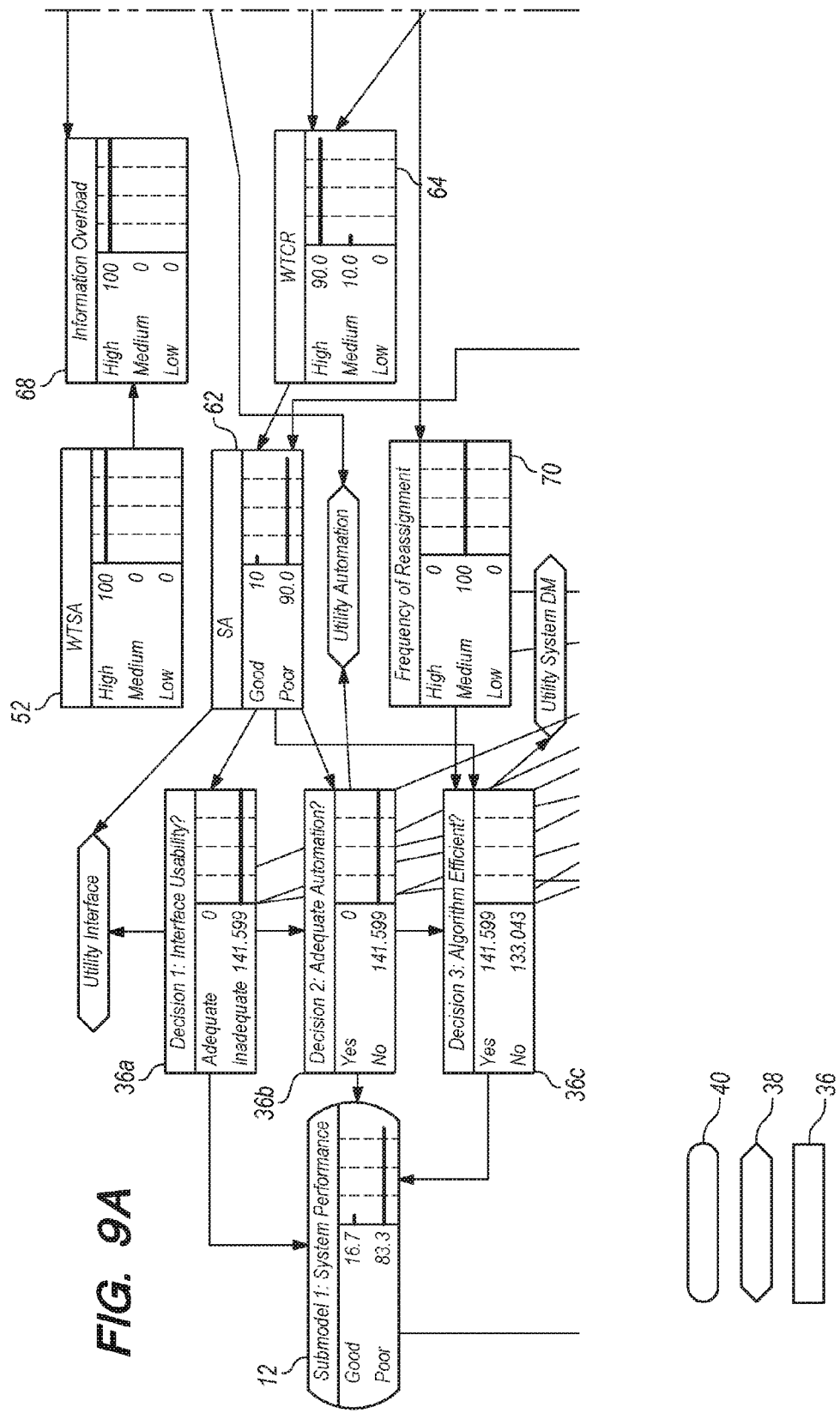
FIG. 9A shows the portion of the network of FIG. 5 related to the algorithm efficiency decision node once the adequate automation node of FIG. 8A has been updated.

FIG. 9 (FIGS. 9A-9B) can display the net for the systems and methods of the present invention once that the decision maker has entered his/her decision outcome for the second decision node 36b (Adequate Automation). Notice that the probabilities for each status of the third decision node (Algorithm Efficient) have been recomputed based in the scenario specific frequency of reassignment variable 70 (and nodes 36a and 36b has been recomputed and repopulated). In FIG. 8, the net is recommending that the algorithm is not efficient (142% versus 133%).

Figure 10A:
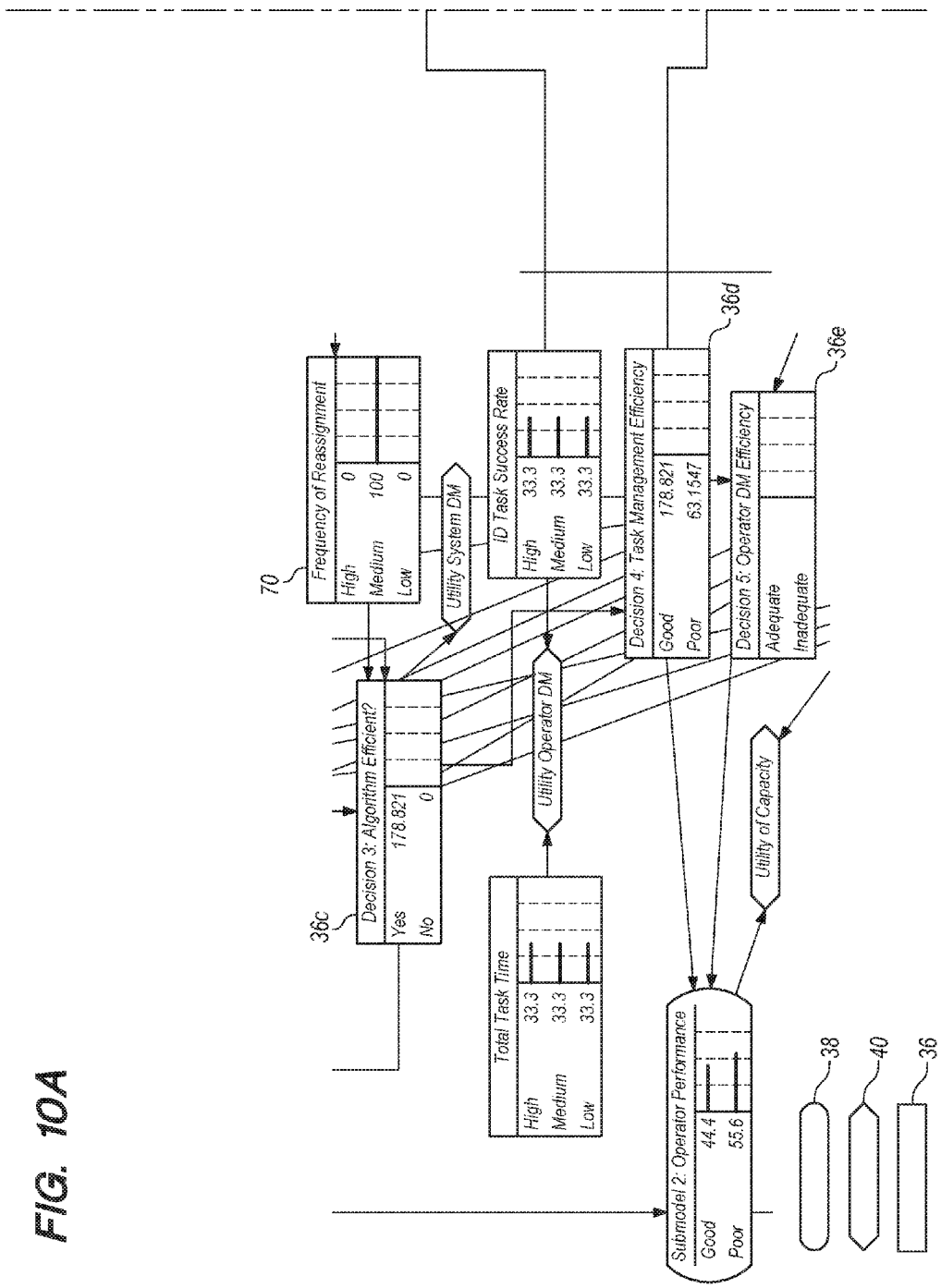
FIG. 10A shows the portion of the network of FIG. 5 related to the task management efficiency node once the algorithm efficiency node of FIG. 9A has been updated.
Figures 10, 10B:
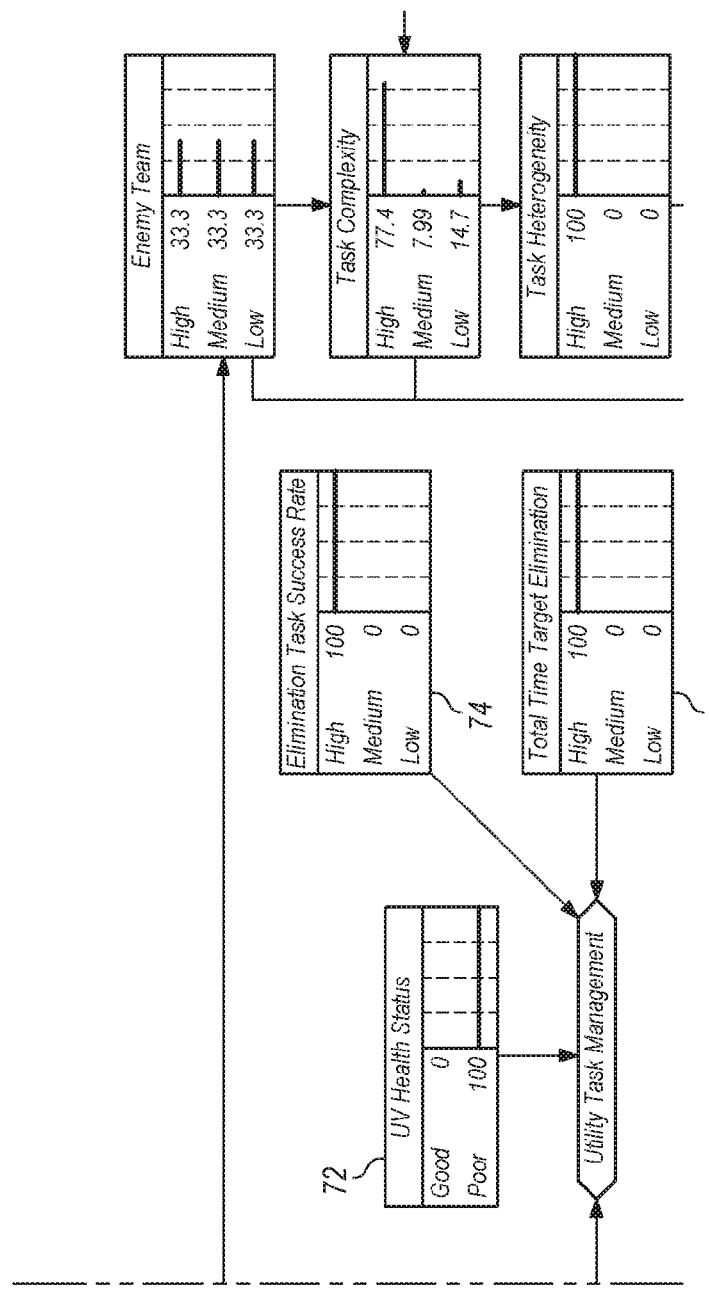
FIG. 10B shows updated probability tables based on the task management efficiency node population of FIG. 10A.

FIG. 10 (FIGS. 10A-10B) can display the computed probabilities for the fourth decision node (Task Management Efficiency). These probabilities are shown only after the decision maker has entered a decision in the third decision node 36c (Algorithm Efficient-once a decision has been entered, the node goes from 50/50 to 100/0). Notice that observations have been entered in nodes that influence the fourth decision node 36d (these observations are UV Health Status 72, Elimination Task Success Rate 74 and Total time for Target Elimination 76, as shown in FIG. 10). Also notice, as the decision maker goes down in the hierarchical decision making process, the final percentage shown in each decision node once the decision maker has entered his/her input fluctuates as a results of new observations being added to the net and as input is entered in the decision nodes for the hierarchical decision making process (i.e., compare second decision node 36*b* of 142% in FIG. 5 with third decision node 36*c* of 178%).

Figure 11:
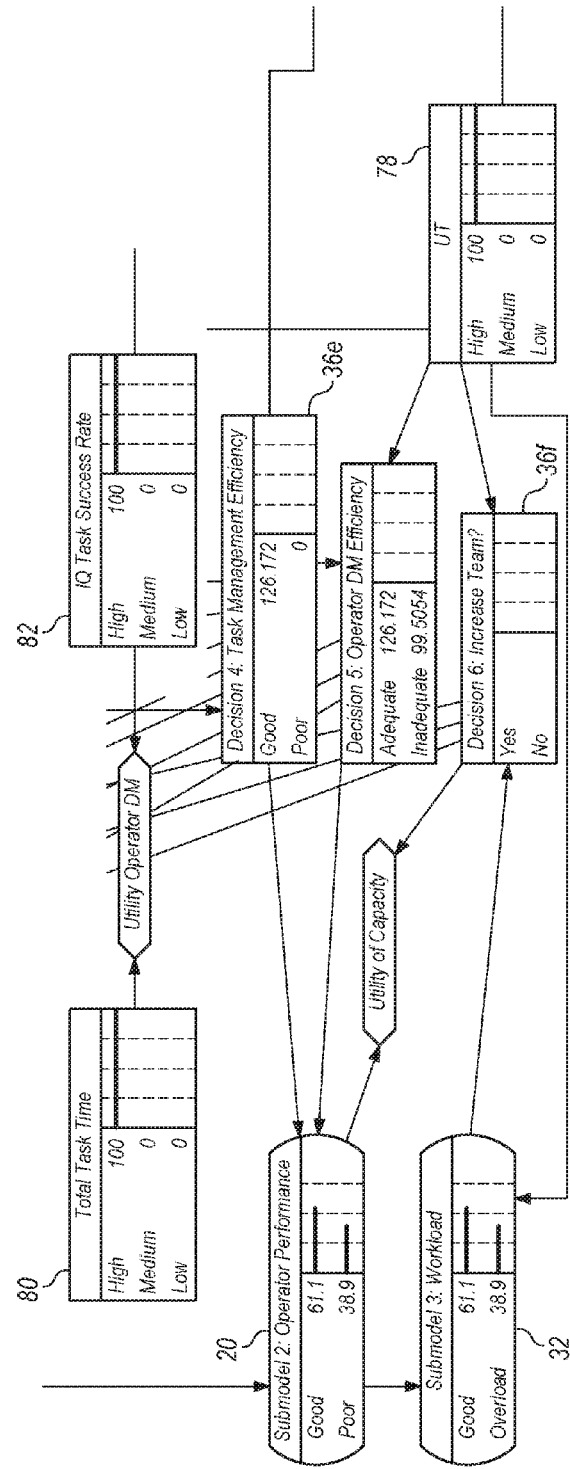
FIG. 11 shows the portion of the network of FIG. 5 related to the operator DM efficiency decision node.

FIG. 11 can display the results of the net of the present invention once the decision maker has entered an outcome for the fourth decision node (Task Management Efficiency) and the observations have been entered in the related nodes (UT 78, Total Task Time 80, ID scenario specific variable of Task Success Rate 82 is input, as shown in FIG. 11). Notice that the net now displays the computed probabilities for the fifth decision node 36*e* (Operator DM Efficiency).

Figure 12:
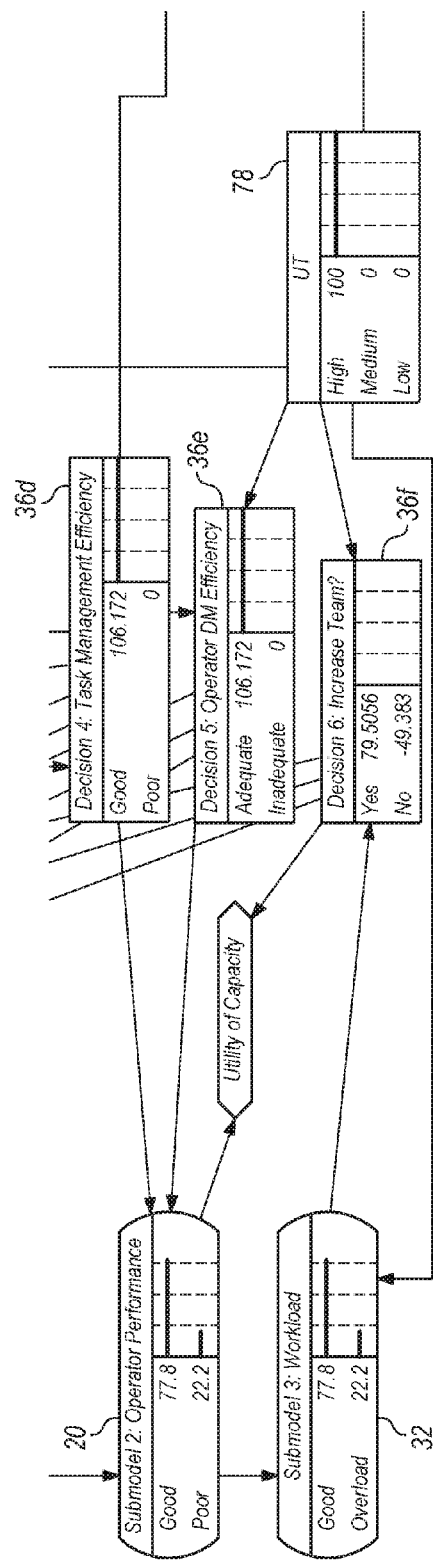
FIG. 12 shows the portion of the network of FIG. 5 related to increase team decision node.

FIG. 12 displays the results of the net once that the decision maker has entered an outcome for the fifth decision node 36*e* (Operator DM Efficiency). Notice that the probabilities for the last decision node 36*f*, Increase Team are not being displayed.

Figure 13A:
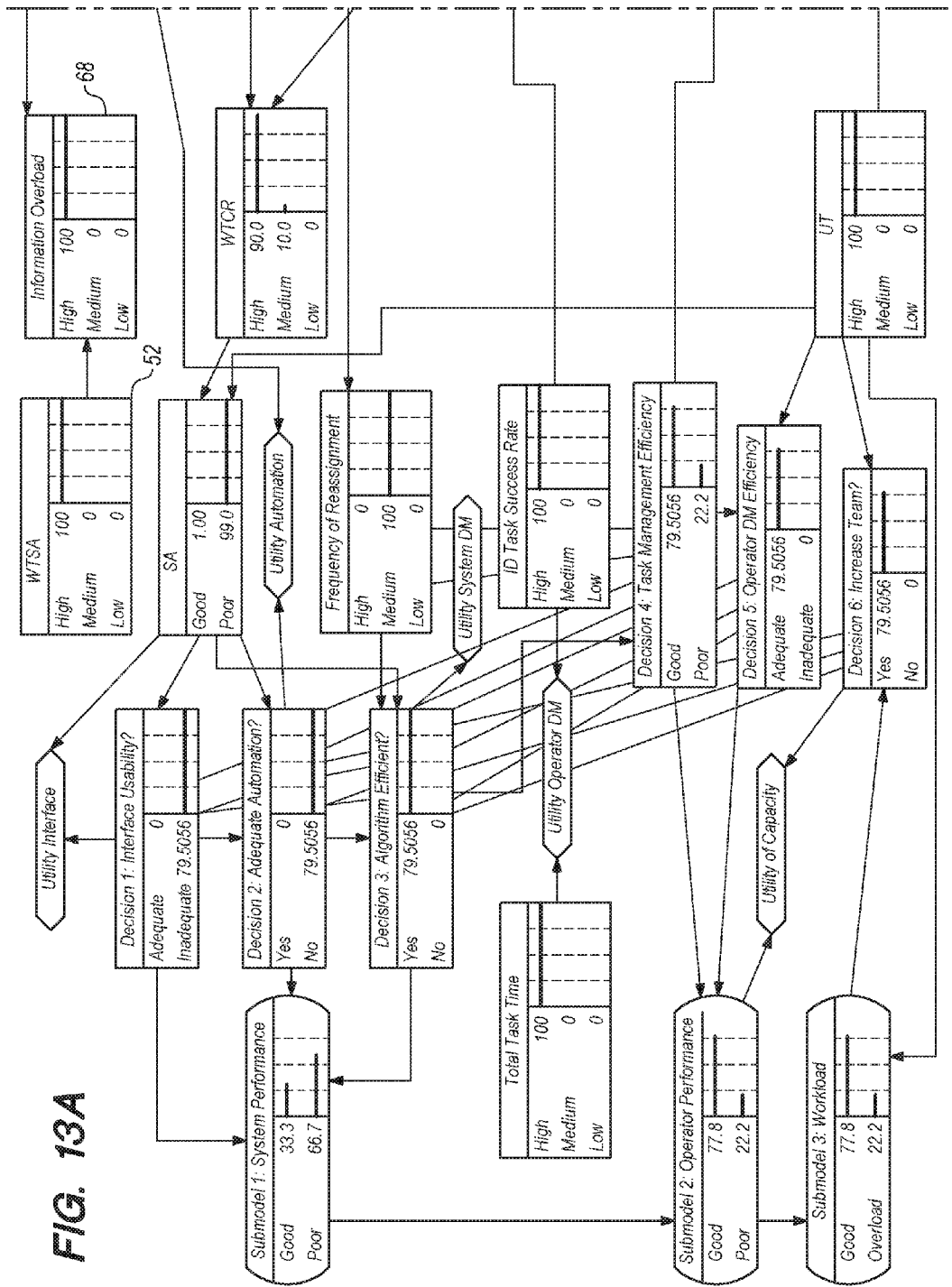
FIG. 13A shows the network of FIG. 5 once the tool has accomplished its predictive function and data for the increase team nodes has been input.

FIG. 13 (FIGS. 13A-13B) can display the results of the net once that the decision maker has entered the outcome of the final decision. FIG. 13 also displays the final view of the entire net once that all the observed nodes and the decision maker inputs (decisions for each node) have been entered in each decision node prediction. From this final view the operator can also make evaluations into what causes the outcome of the decisions. In this particular example, it can be observed that even though the system performance was poor somehow the operator make up for the poor design. From observing the final view of the decision net, system engineers can conclude that design areas such as interface design and level of automation need to be reviewed in order to increase Situation Awareness and decrease WTSA 52, Information Overload 68, IT 54 and WTQ 58.

6. Model Validation and Data Collection

Since there is no test bed available that portrays all the complexities of a futuristic mission scenario, the Research Environment for Supervisory Control of Heterogeneous Unmanned Vehicles (RESCHU) developed by MIT was later modified to be used as a test bed to be used to validate the systems and methods of the present invention. The RESCHU simulator is a test bed that can allow operators to supervise a team of Unmanned Aerial Vehicles (UAVs) and Unmanned Underwater Vehicles (UUVs) while conducting surveillance and identification tasks. This simulation was modified for this study to include the following requirements: 1) a complex mission scenario with an asset to protect and multiple simultaneous enemies to attack, 2) a highly automated system that used mission definition language (MDL) and 3) a highly heterogeneous team that is made of at least three different types of UVs. The new version of the simulation is called RESCHU SP.

It is important to mention that the UV technology selected as an example of NCO technology that can allow one operator to supervise multiple UVs can be the Collaborative Sensing Language (CSL), which was developed at the University of California, Berkeley. The CSL is a high-level feedback control language for mobile sensor networks of UAVs. This system can allow an operator to concentrate on high-level decisions, while the system takes care of low-level decisions, like choosing which UV to send for a particular type of task. A framework for the CSL was designed to integrate CSL into the complex mission scenario portrayed by the RESCHU SP simulator. The CSL version displayed in this simulation is only intended to illustrate one way to portray how this technology may work in more complex mission scenarios and with supervisory control of heterogeneous UVs (See FIG. 23). However, other software with similar functionality can be used to validate the systems and methods of the present invention.

a. Vehicle Types and Functions

The team of UVs in the RESCHU SP simulator can be composed of UAVs 104, USVs 106, and UUVs 108. There are two types of UAVs 104, the MALE (Medium Altitude, Long Endurance) UAV and the HALE (High Altitude, Long Endurance) UAV; both can travel to areas of interest to detect potential enemies. When a UAV 104 detects a potential enemy, a USV 106 can be sent to the detection area to identify the vehicle (i.e., the unidentified vehicles appear as dark yellow numbered icons in map). Engaging the video payload that arrives at a detection area requires the operator to decide whether the vehicle detected is a potential enemy. If an enemy is identified, a UUV travels to the location to target the enemy. UUVs are slower than USVs and UAVs. UAVs are the fastest UVs.

Figure 14:
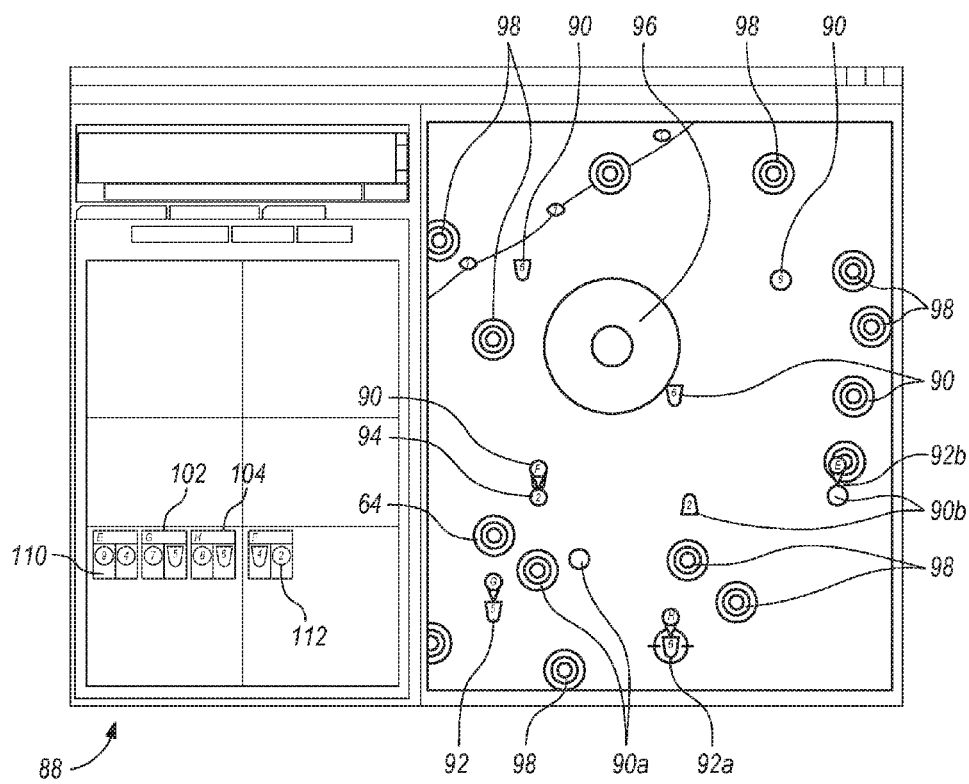

Referring now to FIG. 14, FIG. 14 can be a screen shot 88 that can display RESCHU SP simulation of a mission scenario with a team size of nine UVs (icons 90 on the map), three potential enemies (icons 92 on the map), and one identified enemy (icon 94 on the map). Notice the big circle 96 in FIG. 14 can be the asset to protect (an oil platform, while the big circles 98 can represent threat areas that the UVs should avoid. The CSL tab shows how the technology handles missions. In the Active section of the tab, identify and attack missions that currently active are displayed. For example, the Identify Missions box (icon 110) in screen shot 88 can display a mission to identify potential enemy 92*a* using a particular USV (such as USV represented by icon 90*a*, for example). Similarly, in the Attack Missions section of FIG. 14, icon 112 can display a mission to attack identified 92*b* using USV 90*b*. Other pairings could of course also be represented in screen shot 88.

b. Operator Tasks

For screen shot 88, the operator's main task can be to identify and target potential enemies while protecting an asset (i.e., oil platform). At the same time, the operator is responsible for supervising the path of the UVs, in order to avoid traveling through potential threat areas 98 in FIG. 14. Threat areas are zones that operators should avoid in order to protect the health of their vehicles. Moreover, operators are also responsible for following chat messages which provide them with the necessary Intelligence and guidance to complete their missions.

When a UAV (icon 90) detects a potential enemy 92, a visual flashing alert can be issued to warn the operator. This alert indicates that the operator should command the CSL system to assign a UV to complete the task. For the systems and methods of the present invention, the operator can command the CSL to complete the task through a right-click interaction. The CSL system chooses a UV that is appropriate for the task and one that is also in close proximity to the potential target. The operator is in charge of approving the CSL selection by submitting the task through the Submit All button in the CSL Editing Controls tab.

In the case of multiple identification tasks submitted to the CSL at the same time, the operator's task is to approve the CSL selection, and if applicable, determine the order in which the tasks should be conducted. For example, in a situation in which there is only one UV available for the task, the operator has to determine the order in which tasks should be conducted to ensure a good mission performance. Once the order of tasks has been determined, the operator needs to submit the commands so that the CSL can complete the tasks.

Once that a task has been submitted, a selected UV is sent to location, when it arrives, a visual flashing alert warns the operator that the video payload is ready to engage. Then, the operator engages the video payload through a right-click interaction. The detected vehicle is viewed through the video image displayed in the Payload View tab to determine whether the detection is identified as the enemy. The operator identifies the vehicle by clicking on the Yes or No button below the payload view. A supervisor will inform the operator via chat whether the identification is correct or not. If the operator correctly identifies the vehicle as an enemy, the vehicle icon on the map becomes red. If the operator incorrectly identifies a detected vehicle as the enemy, the supervisor will override the operator; therefore, the icon will not change to red.

The next step for the operator is to inform the CSL that a vehicle should be assigned to complete the target mission. Once again, the CSL system chooses a UV and sends it to the target location. When on target, a visual flashing alert is issued to inform the operator that the UV is ready to engage. The operator confirms this through a right-click interaction, and the target is eliminated. In this way, the operator is responsible to identify all detections and eliminate all enemies in order to protect the asset.

c. Participants and Experimental Procedure

Experiments are being conducted using the RESCHU SP test bed in order to provide data for model validation. The experiment was designed to generate a large data set suitable for model validation. The recruited participants are students from the Naval Postgraduate School (NPS). The online test bed includes: a background and exit survey, an interactive tutorial, a practice trial, and one of a set of possible experimental conditions.

Experiments were designed to be completed in two phases: 1) the software and performance measures program verification phase, and 2) the model validation phase. First, it is desired to ensure that the requirements of the simulation and performance measures computation program are met. Second, it is desired to obtain data associated with the different levels of team size, in order to build confidence in the model's accuracy at replicating human-UV-interaction under different conditions. Having team size as the independent variable, the model's ability to replicate statistically significant effects on the operator performance and/or mission performance could be evaluated. Finally, having data sets associated with the different levels of team size can allow for predictive validation by selecting a single data set associated with one of the conditions and predicting the results observed for a second condition. The recruited participants for the first experimental phase are students from the Naval Postgraduate School (NPS). The online test bed includes: a background and exit survey, an interactive tutorial, a practice trial, and one of a set of possible experimental conditions.

In order to ensure the validity of the variables and relationships represented in the model, the decision network was converted into a Bayesian Belief Network (BBN) to run validation analysis. The software's Test with Cases analysis will be used to validate the network in the second phase of the experiments. The Test with Cases analysis examines if the predictions in the network match the actual cases. The goal of the test is to divide the nodes of the network into two types of nodes: observed and unobserved. The observed nodes are the nodes read from the case file, and their values are used to predict the unobserved nodes by using Bayesian belief updating. The test compares the predicted values for the unobserved nodes with the actual observed values in the case file and the successes and failures are then recorded. The report produced by this analysis has different measures that validate each node's predicted capabilities. After evaluating the validity of the model, we can determine which relationships are incorrect and we can make the network learn those relationships through the collected cases. Finally, we can run sensitivity analysis and predictive validation analysis to determine which variable has the biggest effect on team size and how each variable affects the overall result of the model.

The study design is a between-subject design with three conditions: high team size, medium team size, and low team size. The high team size condition can be composed of 9 UVs: 3 UAVs, 3 USVs and 3 UUVs. The medium team size condition is composed of 7 UVs: 3 UAVs, 2 USVs and 2 UUVs. Finally, the low team size condition is composed of 5 UVs: 3 UAVs, 1 USV and 1 UUV. Notice that the UAV's number was kept constant through the different conditions because the UAVs produce little interaction with the operator (i.e., UAVs only patrol for detection and operators only have to supervise their flight path to avoid flying into threat areas 98). The number of USVs and UUVs was gradually incremented to investigate how they affect the performance measures and therefore the model outcome. Furthermore, the baseline of a team of 5 UVs was decided after pilot testing the simulation with different team sizes.

The experimental test bed was designed for a web-based delivery, with an interactive tutorial and practice trial. A web-based experimentation was chosen in order to obtain as much data as possible. Data collected from the simulation is being recorded to an online database. Demographic information is collected via a background survey presented before the tutorial. Participants are instructed to maximize their overall performance by: 1) Avoiding threat areas that dynamically changed and therefore minimizing damage to the UVs; 2) Correctly identifying enemies; 3) Targeting enemies before they reach the asset; 4) Overriding the system when necessary to minimize vehicle travel times and maximize mission performance; and, 5) Eliminating potential enemies as soon as possible.

In one embodiment, the computer model tool can allow the user to set requirements to optimize the outcome of the decision tool; therefore, allowing the model to compute the right recommendation based on these requirements.

The model captures operator and system performance measures, and uses them to interpret results in a quantitative and qualitative manner which is easy to understand for the decision maker and/or the system designer. No previous models were able to capture the qualitative information about the relationship between the variables. The model can allow a wide range of analyses to be easily run through the use of the NETICA software. These analyses include: Test with Cases Analysis, Sensitivity Analysis, Predictive Analysis, etc.

The model provides a better understanding of the situation and of how operator capacity is affected by the situation and the system performance. Further, the model can allow a more reliable computation of Situation Awareness and Workload through the use of new variables that are correlated to these measures and their relationships to these and other variables. Still further, the model can allow trust to be measured. Trust has been referred to as a vital variable that should be considered in future models.

The model can allow evaluation of not only the new technology being tested but the system as a whole. In the timeline developed from data, one can see how efficient and automated are the UV themselves, and how efficiently the system design handles each event (we code measures by events and therefore can see the specific details of each—events are basically tasks to be done in the simulation. Other embodiments could add a timeline view of the data to users.

The model helps the designer to evaluate: 1) How potential design modifications to an existing technology will affect overall performance and size of the team; 2) How to understand limitations of future technology in terms of defining system boundaries; and, 3) How to replicate current observed behavior, in order to help diagnose inefficiencies.

The invention was designed to evaluate a team of heterogeneous Unmanned Vehicles; however, it can also be used to evaluate technologies in homogenous UV teams. Moreover, while the model was developed to test technologies in complex mission scenarios it can easily be modified to fix the requirements of a wide range of scenarios.

The model can be easily converted into a dynamic Bayesian network that works as a warning system that alarm operators that the situation is getting too complex and therefore recommends the use of a different system's automation level or recommends requesting help from another UV operator. Linking the model to real time physiological measures of workload, stress and fatigue could also be easy to incorporate, in order to develop an effective warning system for UV systems in complex mission scenarios.

The supervisory control problems that are part of this model are best suited for scenarios that require knowledge-based behaviors and divided attention such as air traffic control scenarios. Therefore, the data gather from the experiment can also be use to develop displays for air traffic control or any other similar scenarios.

The computer tool can be used by C2 designers developing UV systems, as well as designers developing other types of highly automated systems. Moreover, the computer tool could be used as a warning tool that will alert users when they are being overloaded, and that gets its input not only from performance measures, but also from accurate physiological measures or workload, situation awareness, and stress.

The use of the terms "a" and "an" and "the" and similar references in the context of describing the invention (especially in the context of the following claims) is to be construed to cover both the singular and the plural, unless otherwise indicated herein or clearly contradicted by context. The terms "comprising", "having", "including" and "containing" are to be construed as open-ended terms (i.e., meaning "including, but not limited to,") unless otherwise noted. Recitation of ranges of values herein are merely intended to serve as a shorthand method of referring individually to each separate value falling within the range, unless otherwise indicated herein, and each separate value is incorporated into the specification as if it were individually recited herein. All methods described herein can be performed in any suitable order unless otherwise indicated herein or otherwise clearly contradicted by context. The use of any and all examples, or exemplary language (e.g., "such as") provided herein, is intended merely to better illuminate the invention and does not pose a limitation on the scope of the invention unless otherwise claimed. No language in the specification should be construed as indicating any non-claimed element as essential to the practice of the invention.

Preferred embodiments of this invention are described herein, including the best mode known to the inventors for carrying out the invention. Variations of those preferred embodiments may become apparent to those of ordinary skill in the art upon reading the foregoing description. The inventors expect skilled artisans to employ such variations as appropriate, and the inventors intend for the invention to be practiced otherwise than as specifically described herein. Accordingly, this invention includes all modifications and equivalents of the subject matter recited in the claims appended hereto as permitted by applicable law. Moreover, any combination of the above-described elements in all possible variations thereof is encompassed by the invention unless otherwise indicated herein or otherwise clearly contradicted by context.

What is claimed is:

1. A method for predicting, by a computer decision tool given a plurality of operators, a plurality of unmanned vehicles and a given mission, said computer decision tool including a system performance module, an operator performance module, and a workload module, an adequate ratio of the plurality of unmanned vehicles to the operators, the method comprising the steps of:
    A) determining effectiveness of a user interface by an interface usability decision node;
    B) using the results of said step A) to determine whether there is an adequate level of automation by an adequate automation level decision node;
    C) using the results of said step B) to determine algorithm efficiency by an algorithm efficiency decision node;
    D) using the results of said step C) to determine an operator task management efficiency by an operator task management efficiency decision node;
    E) using the results of said step D) to determine an operator decision making efficiency by an operator decision making efficiency decision node;
    F) providing, by the system performance module, a system performance status signal responsive to an output from the interface usability decision node, an output from the adequate automation level decision node, and an output from the algorithm efficiency decision node;
    G) providing, by the operator performance module, responsive to an output from the task management efficiency decision node and an output from the operator decision making efficiency decision node, an operator performance status signal;
    H) providing, by the workload module, a team size decision signal representing the predicted adequate ratio of the unmanned vehicles to the operator, the team size decision signal indicating whether to change a team size of the unmanned vehicles, responsive to an increase team size decision output from an increase team size decision node and responsive to the system performance and operator performance status signals, allowing optimal allocation of unmanned vehicles and operator resources; and,
    said step H) occurring before the mission occurs, to allow for deployment of the plurality of operators and the team size sufficient to accomplish the mission.

2. The method of claim 1 wherein said step A) is calculated using outputs of nature and utility nodes, and wherein as decisions are made by said decision nodes are populated and repopulated with probabilities.

3. In a system for controlling a team of unmanned vehicles and at least one operator, a computer decision tool for predicting an optimum ratio of the unmanned vehicles to the at least one operator for a given mission, the computer decision tool comprising:

a system performance module configured to provide a system performance status signal responsive to an interface usability decision output from an interface usability decision node, an adequate automation decision output from an adequate automation decision node, and an algorithm efficiency decision signal output from an algorithm efficiency decision node;

an operator performance module configured to provide an operator performance status signal responsive to a task management efficiency decision output from a task management efficiency decision node and an operator decision making efficiency decision output from an operator decision making efficiency decision node; and, a workload module configured to provide a team size decision signal representing the predicted adequate ratio of the unmanned vehicles to the operator for the mission, the team size decision signal indicating whether to change a team size of the unmanned vehicles, responsive to an increase team decision output from an increase team decision node and responsive to the system performance and operator performance status signals, allowing optimal allocation of unmanned vehicles and operator resources before the mission occurs.

4. The decision tool of claim 3, including:

a utility node for each decision node;

multiple nature nodes including;

observable nature nodes representative of one or more node indications from the node group of Total Task Time, Wait Times due to Loss of Situation Awareness (WTSA), Frequency of Reassignment, ID Task Success Rate, Neglect Time (NT), System Interruption, UV Health Status, Utilization Time (UT), Interaction Times (IT), Wait Times due to Queue (WTQ), Elimination Task Success Rate, Total time to Target Elimination, Team Heterogeneity and Team Size nodes; and unobservable nature nodes representative of one or more node indications from the group of System Performance, Operator Performance, Workload, Situation Awareness (SA), Information Overload, Automation level, Enemy Team, Task Complexity and Task Heterogeneity nodes.

* * * * *